United States Patent
Schultz et al.

(10) Patent No.: US 11,298,244 B2
(45) Date of Patent: Apr. 12, 2022

(54) INTERBODY IMPLANTS AND INSTRUMENTATION

(71) Applicant: K2M, Inc., Leesburg, VA (US)

(72) Inventors: Christian Karl Schultz, Hoboken, NJ (US); Bryan D. Milz, Florida, NY (US); Zinoviy Sosnov, Fair Lawn, NJ (US); Brian Haight, Sussex, NJ (US); Justyna Zielinska, Linden, NJ (US); Shawn Graham, Morristown, NJ (US)

(73) Assignee: K2M, Inc., Leesburg, VA (US)

( * ) Notice: Subject to any disclaimer, the term of this patent is extended or adjusted under 35 U.S.C. 154(b) by 147 days.

(21) Appl. No.: 16/775,672

(22) Filed: Jan. 29, 2020

(65) Prior Publication Data

US 2020/0246162 A1    Aug. 6, 2020

Related U.S. Application Data

(60) Provisional application No. 62/799,360, filed on Jan. 31, 2019.

(51) Int. Cl.
*A61F 2/46* (2006.01)
*A61F 2/44* (2006.01)
(Continued)

(52) U.S. Cl.
CPC ........ *A61F 2/4611* (2013.01); *A61B 17/1757* (2013.01); *A61F 2/30749* (2013.01); *A61F 2/442* (2013.01)

(58) Field of Classification Search
CPC ........ A61B 17/1757; A61F 2/44; A61F 2/442; A61F 2/4455; A61F 2/446; A61F 2/4465;
(Continued)

(56) References Cited

U.S. PATENT DOCUMENTS 5,645,084 A    7/1997  McKay
5,669,909 A    9/1997  Zdeblick et al.
(Continued)

FOREIGN PATENT DOCUMENTS

EP    2865347 A1    4/2015
WO    2010011849 A1    1/2010
WO    2012141715 A1    10/2012

OTHER PUBLICATIONS

European Search Report for EP20154502.7 dated Jul. 10, 2020; 3 pages.
(Continued)

*Primary Examiner* — Eric S Gibson
(74) *Attorney, Agent, or Firm* — Lerner, David, Littenberg, Krumholz & Mentlik, LLP

(57) ABSTRACT

In some embodiments, the present disclosure relates to a system that includes an insertion tool and a drill guide. The insertion tool includes a body with a distal portion and a distal end. The body has a first engagement feature extending longitudinally along the distal portion and two arms extending longitudinally from the distal end of the body. The drill guide includes two bores and an open faced channel therebetween. The open faced channel includes a second engagement feature slidably engageable with the first engagement feature on the body of the insertion tool. The two bores are adapted for the disposal of a fastener driver tool therethrough.

20 Claims, 19 Drawing Sheets

(51) Int. Cl.
*A61B 17/17* (2006.01)
*A61F 2/30* (2006.01)

(58) Field of Classification Search
CPC .......... A61F 2/447; A61F 2/46; A61F 2/4603; A61F 2/4611; A61F 2002/4622; A61F 2002/4625; A61F 2002/4627
See application file for complete search history.

(56) References Cited

U.S. PATENT DOCUMENTS

| | | | |
|---|---|---|---|
| 5,782,919 A | 7/1998 | Zdeblick et al. |
| 5,984,967 A | 11/1999 | Zdeblick et al. |
| 6,086,614 A | 7/2000 | Mumme |
| 6,193,721 B1 | 2/2001 | Michelson |
| 6,206,922 B1 | 3/2001 | Zdeblick et al. |
| 6,235,033 B1 | 5/2001 | Brace et al. |
| 6,245,072 B1 | 6/2001 | Zdeblick et al. |
| 6,258,089 B1 | 7/2001 | Campbell et al. |
| 6,306,139 B1 | 10/2001 | Fuentes |
| 6,331,179 B1 | 12/2001 | Freid et al. |
| 6,375,655 B1 | 4/2002 | Zdeblick et al. |
| 6,447,512 B1 | 9/2002 | Landry et al. |
| 6,471,724 B2 | 10/2002 | Zdeblick et al. |
| 6,485,517 B1 | 11/2002 | Michelson |
| 6,524,312 B2 | 2/2003 | Landry et al. |
| 6,558,423 B1 | 5/2003 | Michelson |
| 6,595,995 B2 | 7/2003 | Zdeblick et al. |
| 6,613,091 B1 | 9/2003 | Zdeblick et al. |
| 6,645,206 B1 | 11/2003 | Zdeblick et al. |
| 6,695,845 B2 | 2/2004 | Dixon et al. |
| 6,695,851 B2 | 2/2004 | Zdeblick et al. |
| 6,730,127 B2 | 5/2004 | Michelson |
| 6,749,636 B2 | 6/2004 | Michelson |
| 6,884,242 B2 | 4/2005 | LeHuec et al. |
| 6,890,355 B2 | 5/2005 | Michelson |
| 6,902,565 B2 | 6/2005 | Berger et al. |
| 6,964,664 B2 | 11/2005 | Freid et al. |
| 6,972,019 B2 | 12/2005 | Michelson |
| 6,989,031 B2 | 1/2006 | Michelson |
| 7,033,394 B2 | 4/2006 | Michelson |
| 7,041,135 B2 | 5/2006 | Michelson |
| 7,131,974 B2 | 11/2006 | Keyer et al. |
| 7,163,561 B2 | 1/2007 | Michelson |
| 7,175,624 B2 | 2/2007 | Konieczynski et al. |
| 7,238,186 B2 | 7/2007 | Zdeblick et al. |
| 7,288,094 B2 | 10/2007 | Lindemann et al. |
| 7,294,134 B2 | 11/2007 | Weber |
| 7,300,440 B2 | 11/2007 | Zdeblick et al. |
| 7,306,605 B2 | 12/2007 | Ross |
| 7,309,340 B2 | 12/2007 | Fallin et al. |
| 7,318,825 B2 | 1/2008 | Butler et al. |
| 7,435,262 B2 | 10/2008 | Michelson |
| 7,442,209 B2 | 10/2008 | Michelson |
| 7,455,692 B2 | 11/2008 | Michelson |
| 7,527,629 B2 * | 5/2009 | Link ................. H05K 13/0812 606/87 |
| 7,527,639 B2 | 5/2009 | Orbay et al. |
| 7,537,663 B2 | 5/2009 | Phelps et al. |
| 7,537,664 B2 | 5/2009 | O'Neill et al. |
| 7,540,882 B2 | 6/2009 | Michelson |
| 7,608,080 B2 | 10/2009 | Shipp et al. |
| 7,611,536 B2 | 11/2009 | Michelson |
| 7,618,418 B2 | 11/2009 | Malandain |
| 7,621,958 B2 | 11/2009 | Zdeblick et al. |
| 7,635,366 B2 | 12/2009 | Abdou |
| 7,637,951 B2 | 12/2009 | Michelson |
| 7,637,954 B2 | 12/2009 | Michelson |
| 7,666,185 B2 | 2/2010 | Ryan et al. |
| 7,674,279 B2 | 3/2010 | Johnson |
| 7,736,380 B2 | 6/2010 | Johnston et al. |
| 7,794,502 B2 | 9/2010 | Michelson |
| 7,811,292 B2 | 10/2010 | Lo et al. |
| 7,875,062 B2 | 1/2011 | Lindemann et al. |
| 7,901,458 B2 | 3/2011 | DeRidder et al. |
| 7,905,886 B1 | 3/2011 | Curran et al. |
| 7,914,561 B2 | 3/2011 | Konieczynski et al. |
| 7,935,137 B2 | 5/2011 | Gorhan et al. |
| 7,935,149 B2 | 5/2011 | Michelson |
| 7,963,982 B2 | 6/2011 | Kirschman |
| 7,981,142 B2 | 7/2011 | Konieczynski et al. |
| 7,985,258 B2 | 7/2011 | Zdeblick et al. |
| 7,988,714 B2 | 8/2011 | Puekert et al. |
| 7,998,215 B2 | 8/2011 | Frey et al. |
| 8,043,343 B2 | 10/2011 | Miller et al. |
| 8,062,342 B2 | 11/2011 | Suh |
| 8,123,788 B2 | 2/2012 | Michelson |
| 8,128,628 B2 | 3/2012 | Freid et al. |
| 8,137,403 B2 | 3/2012 | Michelson |
| 8,167,946 B2 | 5/2012 | Michelson |
| 8,182,518 B2 | 5/2012 | Butler et al. |
| 8,206,399 B2 | 6/2012 | Gill et al. |
| 8,216,316 B2 | 7/2012 | Kirschman |
| 8,231,633 B2 | 7/2012 | Lim et al. |
| 8,287,575 B2 | 10/2012 | Murner et al. |
| 8,298,235 B2 * | 10/2012 | Grinberg ............ A61F 2/4684 606/86 A |
| 8,298,272 B2 | 10/2012 | Edie et al. |
| 8,323,343 B2 | 12/2012 | Michelson |
| 8,328,872 B2 * | 12/2012 | Duffield ................ A61F 2/44 623/17.16 |
| 8,343,220 B2 | 1/2013 | Michelson |
| 8,353,958 B2 | 1/2013 | Edie et al. |
| 8,353,959 B2 | 1/2013 | Michelson |
| 8,398,688 B2 | 3/2013 | Peukert et al. |
| 8,403,986 B2 | 3/2013 | Michelson |
| 8,425,530 B2 | 4/2013 | Winslow et al. |
| 8,491,598 B2 | 7/2013 | Crook |
| 8,491,654 B2 | 7/2013 | Frey et al. |
| 8,540,725 B2 | 9/2013 | Lim et al. |
| 8,562,655 B2 | 10/2013 | Butler |
| 8,636,804 B2 | 1/2014 | Errico et al. |
| 8,641,768 B2 | 2/2014 | Duffield et al. |
| 8,668,741 B2 | 3/2014 | Michelson |
| 8,696,681 B2 | 4/2014 | Harris et al. |
| 8,709,083 B2 * | 4/2014 | Duffield ............ A61F 2/30771 623/17.16 |
| 8,728,387 B2 | 5/2014 | Jones et al. |
| 8,740,983 B1 * | 6/2014 | Arnold ............... A61B 17/8875 623/17.16 |
| 8,795,341 B2 | 8/2014 | Walker et al. |
| 8,808,304 B2 * | 8/2014 | Weiman ................ A61F 2/4455 606/99 |
| 8,864,829 B1 | 10/2014 | Bruffey et al. |
| 8,876,835 B2 | 11/2014 | Petit |
| 8,882,813 B2 * | 11/2014 | Jones ................. A61B 17/7059 606/289 |
| 8,882,814 B2 | 11/2014 | Suh |
| 8,882,843 B2 | 11/2014 | Michelson |
| 8,906,097 B2 | 12/2014 | Mather et al. |
| 8,926,703 B2 | 1/2015 | Michelson |
| 8,945,227 B2 | 2/2015 | Kirschman |
| 9,017,412 B2 | 4/2015 | Wolters et al. |
| 9,028,498 B2 | 5/2015 | Hershgold et al. |
| 9,131,969 B2 | 9/2015 | Lorio et al. |
| 9,173,750 B2 | 11/2015 | Weiman et al. |
| 9,180,010 B2 | 11/2015 | Dong et al. |
| 9,192,419 B2 | 11/2015 | McDonough et al. |
| 9,192,483 B1 | 11/2015 | Radcliffe et al. |
| 9,198,769 B2 | 12/2015 | Perrow et al. |
| 9,237,957 B2 | 1/2016 | Klimek et al. |
| 9,248,027 B2 | 2/2016 | Dunworth et al. |
| 9,248,028 B2 | 2/2016 | Gamache |
| 9,277,943 B2 | 3/2016 | Holly et al. |
| 9,301,854 B2 | 4/2016 | Moskowitz et al. |
| 9,326,861 B2 | 5/2016 | Tott et al. |
| 9,327,359 B2 | 5/2016 | Wotruba |
| 9,351,849 B2 | 5/2016 | Mather et al. |
| 9,358,123 B2 | 6/2016 | McLuen et al. |
| 9,358,127 B2 | 6/2016 | Duffield et al. |
| 9,364,343 B2 | 6/2016 | Duffield et al. |
| 9,381,045 B2 | 7/2016 | Donner et al. |
| 9,381,093 B1 | 7/2016 | Morris et al. |
| 9,402,735 B2 | 8/2016 | McDonough et al. |

(56) References Cited

U.S. PATENT DOCUMENTS

| | | | |
|---|---|---|---|
| 9,427,330 B2 | 8/2016 | Petersheim et al. | |
| 9,445,851 B2 | 9/2016 | Walker et al. | |
| 9,456,901 B2 | 10/2016 | Jones et al. | |
| 9,463,098 B2 | 10/2016 | Michelson | |
| 9,510,957 B2 | 12/2016 | Weiman et al. | |
| 9,585,762 B2 | 3/2017 | Suddaby et al. | |
| 9,615,838 B2 | 4/2017 | Nino et al. | |
| 9,615,936 B2 | 4/2017 | Duffield et al. | |
| 9,675,467 B2 | 6/2017 | Duffield et al. | |
| 9,693,876 B1 | 7/2017 | Mesiwala | |
| 9,757,163 B2 | 9/2017 | Jacene et al. | |
| 9,833,333 B2 | 12/2017 | Duffield et al. | |
| 9,848,996 B2 | 12/2017 | Faulhaber | |
| 9,855,150 B2 | 1/2018 | Altarac et al. | |
| 9,895,237 B2 | 2/2018 | Seifert et al. | |
| 9,913,732 B2 | 3/2018 | Kana et al. | |
| 9,918,848 B2 | 3/2018 | Waugh et al. | |
| 9,987,051 B2 | 6/2018 | Nunley et al. | |
| D824,518 S | 7/2018 | Wilson et al. | |
| 10,028,841 B2 | 7/2018 | Moore et al. | |
| 10,342,678 B2* | 7/2019 | Flores | A61F 2/447 |
| 10,850,193 B2 | 12/2020 | DeRidder et al. | |
| 2003/0149438 A1 | 8/2003 | Nichols et al. | |
| 2004/0010259 A1 | 1/2004 | Keller et al. | |
| 2004/0098129 A1 | 5/2004 | Lin | |
| 2005/0283245 A1 | 12/2005 | Gordon et al. | |
| 2007/0016218 A1 | 1/2007 | Winslow et al. | |
| 2008/0281425 A1 | 11/2008 | Thalgott et al. | |
| 2008/0287957 A1* | 11/2008 | Hester | A61F 2/4611 606/99 |
| 2009/0105831 A1* | 4/2009 | Jones | A61B 17/8042 623/17.16 |
| 2009/0210062 A1 | 8/2009 | Thalgott et al. | |
| 2010/0100138 A1 | 4/2010 | Reynolds et al. | |
| 2011/0264152 A1* | 10/2011 | Weiman | A61B 17/1757 606/86 R |
| 2012/0277803 A1 | 11/2012 | Remesh et al. | |
| 2012/0277870 A1 | 11/2012 | Wolters et al. | |
| 2012/0277873 A1 | 11/2012 | Kana et al. | |
| 2013/0006314 A1 | 1/2013 | Mueller | |
| 2013/0218276 A1 | 8/2013 | Fiechter et al. | |
| 2013/0345813 A1 | 12/2013 | Frank et al. | |
| 2014/0066997 A1 | 3/2014 | Humphreys | |
| 2014/0200670 A1 | 7/2014 | Chin et al. | |
| 2015/0216573 A1 | 8/2015 | Chin et al. | |
| 2015/0328005 A1* | 11/2015 | Padovani | A61F 2/30744 623/17.13 |
| 2015/0328009 A1 | 11/2015 | Zappacosta et al. | |
| 2016/0106553 A1 | 4/2016 | Melkent et al. | |
| 2016/0128737 A1 | 5/2016 | Coric et al. | |
| 2016/0151171 A1* | 6/2016 | Mozeleski | A61B 17/7059 623/17.16 |
| 2016/0213488 A1 | 7/2016 | Moore et al. | |
| 2016/0220388 A1* | 8/2016 | Flores | A61F 2/4611 |
| 2016/0235448 A1* | 8/2016 | Seex | A61F 2/4611 |
| 2016/0235548 A1 | 8/2016 | McLaughlin et al. | |
| 2016/0270920 A1 | 9/2016 | Dawson et al. | |
| 2016/0361177 A1 | 12/2016 | Biedermann et al. | |
| 2017/0189204 A1* | 7/2017 | Riemhofer | A61F 2/4611 |
| 2017/0196606 A1* | 7/2017 | Cianfrani | A61B 17/8042 |
| 2017/0245998 A1 | 8/2017 | Padovani et al. | |
| 2017/0340358 A1* | 11/2017 | Bullard | A61B 17/1757 |
| 2018/0318100 A1* | 11/2018 | Altarac | A61F 2/4455 |
| 2019/0133778 A1 | 5/2019 | Johnston | |
| 2020/0246162 A1* | 8/2020 | Schultz | A61F 2/442 |
| 2021/0077268 A1* | 3/2021 | Struck | A61F 2/4455 |
| 2021/0153879 A1* | 5/2021 | Walsh | A61B 17/1631 |
| 2021/0154022 A1* | 5/2021 | Walsh | A61F 2/4611 |

OTHER PUBLICATIONS

Amendia: Spinal Elements; CERES-C: Stand-Alone Interbody: MM-156, May 17, 2018; Rev. 1; 2 pages.
DePuy Synthes, companies of Johnson & Johnson—Zero-P VA Surgical Technique, 2016, 52 pages.
DePuy Synthes, Part of the Johnson & Johnson Family of Companies—Zero-P and Zero-P chronOS: Zero profile anterior cervical interbody fusion (ACIF) device, 2016, 72 pages.
Globus Medical—COALITION Stand-Alone ACDF System, © 2013, 6 pages.
Globus Medical; Independence MIS: Anterior Lumbar Interbody Fushion System; 2017; 56 pages.
Medacta International; MectaLIF Anterior: Anterior Lumbar Interbody Fushion Device: Apr. 2017; 2 pages.
Medtronic—Divergencetm Stand-Alone Interbody Cage Preoperative planning guide and surgical technique, © 2015, 24 pages.
Nuvasive., Base Interfixated Titanium: Rebuilding Spinal Foundation, 2016, 6 pages.
Nuvasive: Speed of Innovation: Brigade: Standalone ALIF: Surgical Technique; 2015, 28 pages.
Nuvasive; Speed of Innovation—Coroent Small Interlock Stand-alone Cervical Interbody Fixation Designed for Simplicity and Versatility, © 2011, 8 pages.
Precision Spine: Vault C: ACDF System; 2015, 8 pages.
SeaSpine: The Next Wave in Spine Technology—Zuma-C Cervical Stabilization System, © 2011,13 pages.
Spine Smith: IN:C2—Now Open for Fusion; 2012, 2 pages.
Stryker Spine: AVS Anchor-L: Lumbar Cage System; Jul. 2013, 2 pages.
Stryker: Aero-C: Anterior Cervical Interboby and Fixation System; Apr. 2016; 28 pages.
Styrker Spine: AVS Anchor-C Cervical Cage System; 2014; 2 pages.
Unison- C Anterior Cervical Fixation System; 2018, 3 pages.
Zavation Z-Link Cervical; 2018; 13 pages.
Zimmer Biome I - Optio-C® Anterior Cervical PEEK Interbody System Surgical Technique Guide, © 2017, 36 pages.
European Extended Search Report for EP20196447.5 dated Feb. 15, 2021, 3 pages.

* cited by examiner

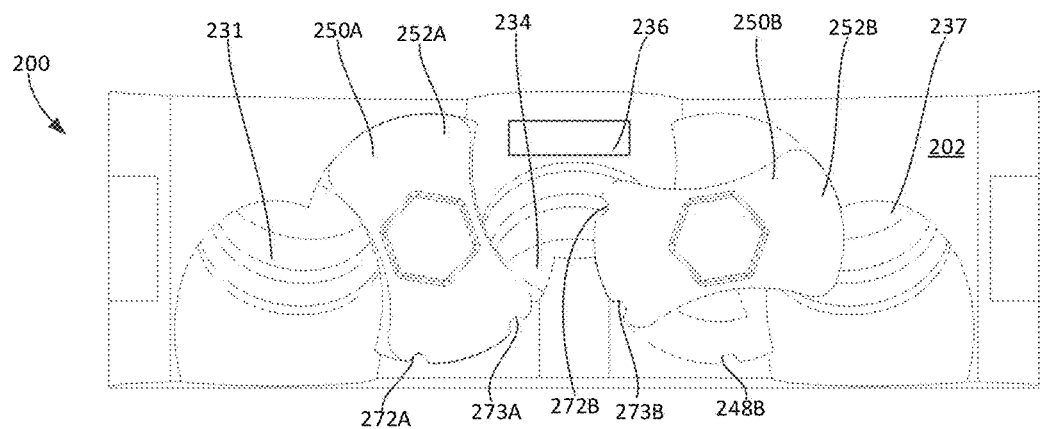
FIG. 20
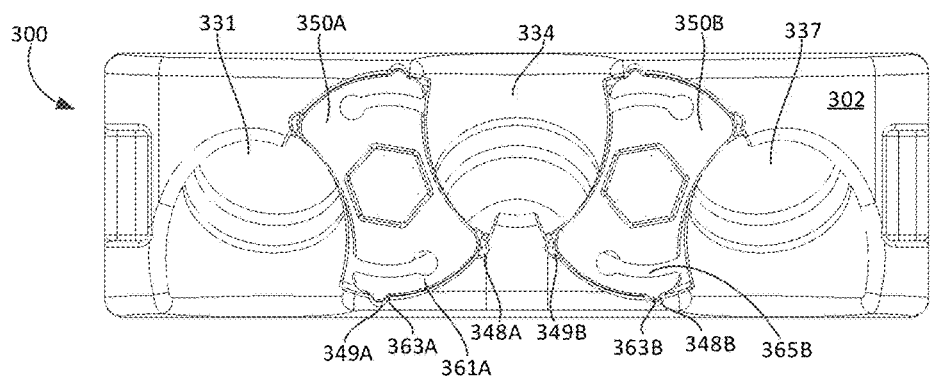
FIG. 21
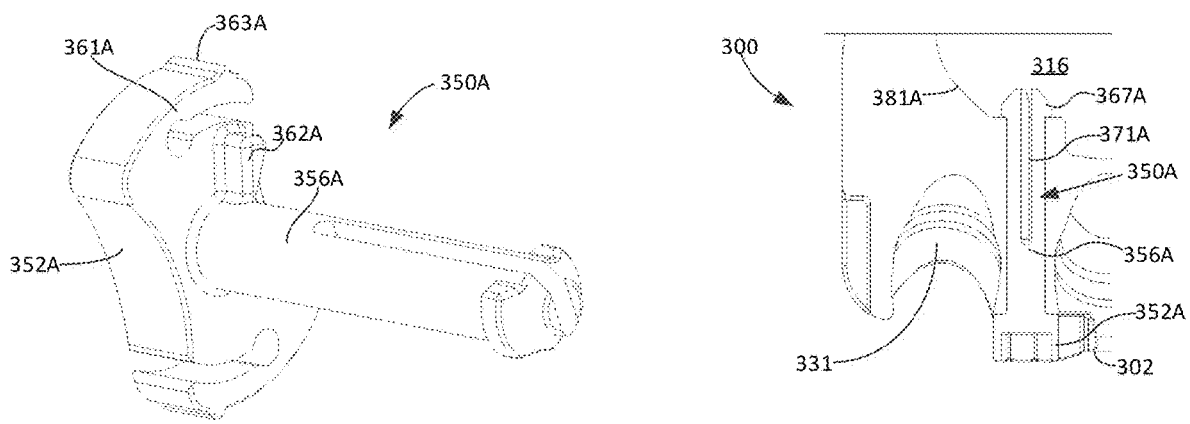
FIG. 22A
FIG. 22B

INTERBODY IMPLANTS AND INSTRUMENTATION

CROSS-REFERENCE TO RELATED APPLICATION

This application claims the benefit of the filing date of U.S. Provisional Patent Application No. 62/799,360, filed Jan. 31, 2019, the disclosure of which is hereby incorporated by reference herein in its entirety.

BACKGROUND OF THE INVENTION

A variety of instruments are often used to advance and place implants into an intervertebral space in the spine as part of a spinal reconstructive surgery. When implants are engaged to certain instruments, a problem may arise in that the implant may be engaged to the instrument upside down. Such a result may occur because the engagement features on each of the instrument and the implant are symmetrical about an axis across a width of the implant, so the implant may be engaged whether it is oriented with a superior side up or an inferior side up. With time, an improper placement of this kind can lead to poor performance of the implant or potentially even failure. Another challenge with implant insertion instruments is that the implant may be unstable or may move relative to instrument while secured to the instrument. This may occur due to a lack of a rotational restraint incorporated into the engagement features on the instrument.

Further, drill guides are often used to aid in the insertion of screws through intervertebral implants to secure the implant to adjacent vertebral bodies. However, such drill guides are typically standalone instruments. As a result, a surgeon requires one instrument to position the implant in the surgical space and another instrument to aid in the seating of screws through the implant and into the bone. This problem of excess instrumentation is exacerbated by the need to have different sizes of insertion instruments and drill guides available, which demands even more instrumentation. Moreover, the more instruments that are utilized, the more instruments ultimately need to be sterilized before additional surgeries can be conducted.

Existing challenges extend to stability of the spinal implants themselves, even when properly placed in an intervertebral disc space. In some instances, forces acting on the implant may cause screws to back out of their positions in the implanted implant. This may lead to poor performance or failure of the implant. Other problems may include limitations on the possible orientations of the implant when inserted into the intervertebral space.

Thus, there is a need to simplify methods of inserting an implant into the spine and to reduce the risk of implant failure after completion of surgery.

BRIEF SUMMARY OF THE INVENTION

In one aspect, the present disclosure relates to a system that includes an insertion tool and a drill guide. In one embodiment, the insertion tool includes a body with a distal portion and a distal end, the body including a first engagement feature extending longitudinally along the distal portion and two arms extending longitudinally from the distal end of the body. The drill guide includes two bores and an open faced channel therebetween, the open faced channel including a second engagement feature slidably engageable with the first engagement feature on the body of the insertion tool. The two bores are adapted for the disposal of a fastener driver tool therethrough.

In some embodiments, the insertion tool may include three prongs that extend longitudinally from the distal end. In some embodiments, the three prongs may include a first prong, a second prong and a third prong. The first prong and the second prong may have equal and opposite shapes and the third prong may have a shape different from each of the first prong and the second prong. In some embodiments, the insertion tool may have a cross-sectional shape distal to the distal end that includes the first, second and third prongs. The cross-sectional shape may be asymmetrical about a first axis across a width of the insertion tool, the first axis parallel to an axis passing through a free end of the first prong and a free end of the second prong.

In some embodiments where the insertion tool includes three prongs, the three prongs may include a first prong and a second prong that are a first length and a third prong that is a second length, the first length longer than the second length. In some embodiments, the first prong may extend to a first free end and the second prong may extend to a second free end, each of the first free end and the second free end including a protrusion thereon.

In some embodiments, the two prongs may be biased inward toward one another. In some embodiments, the first engagement feature may be a pair of slots on opposite surfaces of the body of the insertion tool. To complement the slots, the second engagement feature may be a pair of rails that face one another. Each of the rails is disposable within a respective slot of the body.

In some embodiments, the insertion tool may include an actuatable button on the distal portion of the body. The actuatable button may be biased to protrude relative to the body. In some embodiments, the drill guide may be adapted to slide over the actuatable button while one of the first engagement feature and the second engagement feature is disposed in the other. With the aforementioned features, the drill guide is secured to the insertion tool when positioned in between the actuatable button and the distal end of the body. In some embodiments, the first engagement feature may have a length that extends from a proximal end to a distal end. The distal end of the first engagement feature may be separated from the distal end of the body. In some examples, the body may be cannulated and includes a slidable element disposed therein, the insertion tool being actuatable to advance and retract the slidable element. In some embodiments, the insertion tool may be actuatable to cause forward advancement of the slidable element. Such advancement increasing a spacing between the first arm and the second arm.

In another aspect, the present disclosure relates to an insertion tool. In one embodiment, an insertion tool includes a body with an outer shaft, first and second arms, a pin and an inner shaft. The outer shaft has a length extending from a proximal end to a distal end. The first arm, second arm and pin each extend from the distal end. The distal end has a cross-sectional shape that includes the first arm, the second arm and the pin. The cross-sectional shape is asymmetric about a first axis across a width of the body through its center. The first axis is parallel to a second axis through a free end of the first arm and a free end of the second arm. The inner shaft is disposed within and movable relative to the outer shaft of the body. When the inner shaft moves into contact with the first arm and the second arm, the inner shaft increases a distance between the first arm and the second arm.

In some embodiments, the insertion tool may also include a lever arm attached to the body. The lever arm may be rotatable relative to the body through mechanical coupling of the lever arm to the inner shaft such that actuation of the lever arm causes the inner shaft to move. In some embodiments, the insertion tool may include a lock button attached to the body. The lock button may be adjustable from a closed position to an open position. In the closed position, the lever arm is locked in a fixed position and in the open position, the lever arm is rotatable about an axis through its connection point with the body. In some embodiments, the lock button may be biased in the closed position. In some embodiments, the first arm and the second arm may have a first shape and the pin may have a second shape, where the first shape is different from the second shape. In some embodiments, the first arm and the second arm may be a first length and the pin may be a second length, the first length being longer than the second length. In some embodiments, each of the first arm and the second arm may become larger in size toward their respective free ends such that outward facing surfaces of each arm that face away from each other at the free ends protrude relative to a remainder of each arm.

In another aspect, the present disclosure relates to an intervertebral implant. In one embodiment, the intervertebral implant includes a body, a fastener and a locking element. The body includes a plurality of openings therein. Each of the plurality of openings is accessible from a single side of the body. The fastener is disposed in a first opening of the plurality of openings and the locking element is disposed in a second opening of the plurality of openings. The locking element includes a head, a flexible base abutting the head and a shaft extending from the flexible base. The flexible base and the shaft extend along a longitudinal axis. The flexible base is movable from a first position to a second position. In the first position, the flexible base is secured to the body and has a first perimeter. In between the first position and the second position, a portion of the flexible base is deformed so that the flexible base has a second perimeter smaller than the first perimeter, the first perimeter and the second perimeter measured at the same axial location on the flexible base. The locking element may be movable between a first orientation relative to the body that blocks the first opening and a second orientation relative to the body that does not block the first opening.

In some embodiments, the flexible base may include a flexible bar that extends from a remainder of the flexible base to a free end such that the flexible bar is separated from the remainder of the flexible base by a space. In some embodiments, the flexible bar may include a protrusion that extends outward adjacent to the free end. In some embodiments, the single side of the body may include a first recessed surface sized to receive the head of the locking element and a second recessed surface that is recessed relative to the first recessed surface. The second recess may be sized to receive the flexible base. In some embodiments, the second recessed surface may include a perimeter defined by a first portion with a first radial dimension and a second portion with a second radial dimension smaller than the first radial dimension. The second portion may be interrupted by a first groove and a second groove spaced from one another along a partially circumferential length of the second portion. In some embodiments, when the locking element is disposed in the implant such that the head is disposed on the first recessed surface, the locking element may be rotatable such that the protrusion of the flexible bar is disposable in the first groove and in the second groove. In some embodiments, when the protrusion is disposed in the first groove, a ridge on the base may abut a first end of the first portion of the perimeter of the second recessed surface. Similarly, when the protrusion is disposed in the second groove, the ridge on the base may abut a second end of the first portion of the perimeter of the second recessed surface.

In some embodiments, the remainder of the flexible base separate from the flexible bar may include a longitudinal ridge. In some embodiments, the flexible bar may include a protrusion that extends outward adjacent to the free end and the remainder of the flexible base may include a longitudinal ridge that is positioned opposite the protrusion on a surface of the base. In some embodiments, the space in the flexible base is L-shaped. In some embodiments, the shaft may be a pair of flexible prongs. In some embodiments, the locking element may be located equidistant from upper and lower surfaces of the implant. In some embodiments, the intervertebral implant may include a second locking element that is the same as the first locking element. In some embodiments, the single side of the body may be an anterior side. In some embodiments, the body of the implant may be monolithic.

In one embodiment, an intervertebral implant includes a body, a fastener and a locking element. The body has a plurality of openings therein, each of the plurality of openings being accessible from a first side of the body. The first side of the body has a first recessed surface and a second recessed surface. The fastener is disposed in a first opening of the plurality of openings. The locking element is disposed in a second opening of the plurality of openings, the second opening being located entirely within the second recessed surface. The locking element includes a head, a flexible base abutting the head, and a shaft extending from the flexible base. The flexible base includes a first part and a second part separated from the first part by a third opening. The first part extends to a free end and has a protrusion, while the second part includes a ridge. The shaft extends from the flexible base, and the shaft and the flexible base extend along a longitudinal axis. The flexible base is movable from a first position to a second position such that in the first position, the protrusion is engaged with a groove defined by a boundary between the first recessed surface and the second recessed surface and the ridge abuts a radially oriented edge of the second recessed surface. In the second position, the first part of the flexible base is compressed from a neutral position and is outside of the groove. The locking element is movable between a first orientation relative to the body that blocks the first opening and a second orientation relative to the body that does not block the first opening.

In another aspect, the present disclosure relates to a kit. In one embodiment, the kit includes an insertion tool, a guide structure and an interbody implant. The insertion tool has a body with an end and a plurality of prongs that extend from the end. The guide structure has two bores sized for the placement of fastener driver tool therethrough. The guide structure is engageable with the insertion tool. The interbody implant has two openings on a single side. Each of the two openings is sized to receive at least one of the plurality of prongs of the insertion tool. The insertion tool is adapted to engage with the guide structure and the interbody implant at the same time.

In some embodiments, the plurality of prongs may include three prongs of which two are receivable in a first of the two openings and one is receivable in a second of the two openings. In some embodiments, the insertion tool may include a surface with a longitudinally extending slot and the guide structure may include a longitudinally extending rail. The rail may be disposable in the slot to engage the guide structure with the insertion tool.

In one embodiment, a kit includes an insertion tool, an interbody implant and a graft clip. The insertion tool includes a body with an end and a plurality of prongs that extend from the end. The interbody implant has two openings on a single side, each of the two openings sized to receive at least one of the plurality of prongs of the insertion tool. The graft clip is engageable with the body and is adapted to cover opposing surfaces of the body and the implant when the implant is engaged to the insertion tool. The graft clip includes two arms that are biased toward one another at a distal end of the graft clip.

In some embodiments, each arm may include an outward facing surface with a protrusion thereon.

In another aspect, the present disclosure relates to a method of implanting an interbody implant into a mammalian spine. In one embodiment, the method involves steps including: advancing an end of an insertion tool into an intervertebral implant such that a pair of prongs extending from a distal end of a body of the insertion tool pass through a first opening in the implant and a pin extending from the distal end passes through a second opening in the implant; sliding a drill guide onto the insertion tool and over an actuatable element on the body by displacing the actuatable element from a neutral position; and securing the drill guide to the insertion tool through sliding engagement between a first engagement feature on the drill guide and a second engagement feature on the insertion tool along with advancement of the drill guide distally past the actuatable element so that the actuatable element returns to the neutral position and prevents drill guide from sliding axially in a proximal direction.

In some embodiments, the method may include actuating a control on the insertion tool to advance an inner shaft within the body until the inner shaft is in between the pair of prongs, the advancement of the inner shaft preventing laterally outward facing protrusions on each prong from retreating into the first opening. In some embodiments, actuating the control may include rotating a lever arm attached to the body to cause the inner shaft to advance relative to an outer shaft of the body. In some embodiments, the method includes actuating a detent mechanism in the body to unlock the lever arm and allow rotation of the lever arm.

In some embodiments, sliding of the drill guide over the actuatable element may involve sliding the drill guide over a button on the body adjacent to the distal end, the button depressing when the drill guide is over the button and the button rising when the drill guide is slid distally past the button, the button thereby preventing proximal movement of the drill guide to hold the drill guide in place on the insertion tool.

In another aspect, the present disclosure relates to a method of locking fasteners disposed in an intervertebral implant. In one embodiment, the method involves steps including: inserting an intervertebral implant into an intervertebral disc space between adjacent vertebral bodies in a patient; rotatably advancing a fastener through an opening in the intervertebral implant into a vertebral body adjacent to the intervertebral disc space so that the fastener anchors into the vertebral body; and rotating a locking element disposed in the implant from a first position to a second position, the locking element including a flexible base with an engagement feature that bends to disengage from the first position, wherein in the first position, the opening is unobstructed by the locking element and in the second position, the opening is obstructed by the locking element to prevent back out of the fastener.

In some embodiments, rotation of the locking element may involve disengaging the protrusion from a first groove in a recessed surface of the intervertebral implant. In some embodiments, rotation of the locking element may be limited to a rotational range extending between and including the first position and the second position. In some embodiments, the rotation of the locking element may be limited by a ridge of the locking element abutting a first outer edge or a second outer edge of a recessed surface defining a volume within which the locking element is partially disposed, the first outer edge or the second outer edge blocking further rotation of the locking element in one rotational direction. In some embodiments, the rotation of the flexible base from the first position or the second position to disengage the locking element from the first position or the second position may cause a cross-sectional size of the locking element to decrease.

In some embodiments, the method may include rotation of two locking elements, each locking element rotated in a clockwise direction to obstruct the opening and a second opening. In some embodiments, the method may include inserting the locking element into the implant through a second opening in the implant, the locking element including a flexible shaft that flexes inward during insertion and expands outward once fully inserted to limit axial movement of the locking element.

BRIEF DESCRIPTION OF THE DRAWINGS

The present disclosure will be better understood on reading the following detailed description of non-limiting embodiments thereof, and on examining the accompanying drawings, in which:

FIG. 20 is a side view of an intervertebral implant according to another embodiment of the disclosure.

FIG. 21 is a side view of an intervertebral implant according to another embodiment of the disclosure.

FIGS. 22A and 22B are close up partial views of the intervertebral implant of FIG. 21.

DETAILED DESCRIPTION

Figure 1:
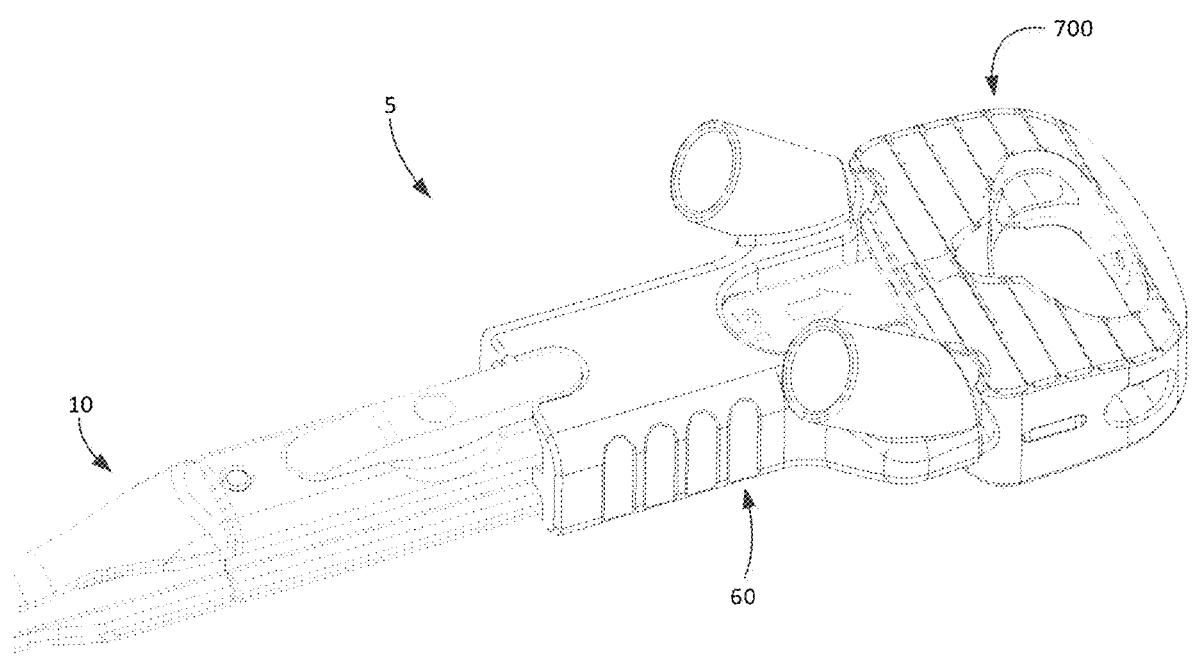
FIG. 1 is a perspective view of an implant insertion system with an intervertebral implant attached according to one embodiment of the disclosure.

The present disclosure generally relates to instruments and implants used to repair and reconstruct a mammalian spine. Instruments described include an insertion tool, a drill guide engageable with the insertion tool, and a graft clip, among others. These instruments are used to improve methods of placing an intervertebral implant within an intervertebral space in a reconstructive surgery. Further, various implants used with such instruments are also described herein. One example of an implant insertion system 5 is shown in FIG. 1 and includes an insertion tool 10 and a drill guide 60. In the illustrated system, an intervertebral implant 700 is secured to the insertion tool. These components improve the ability of a user to engage an implant with an instrument and also improve the ability of the user to properly secure the implant in the correct position within a body of a patient. The use of the term "user" herein should be construed broadly to mean the person or machine (e.g., robot) performing the surgery. This could be, for example, a surgeon.

It should be appreciated that although specific examples provided throughout the disclosure reference spinal surgery and methods involving antero-lateral or lateral approaches to the spine, the principles set forth herein are contemplated for application in other surgical approaches or in other areas of the body where similar access is required and/or where implants with a similar structure are implanted.

As used herein, the terms "proximal" and "distal," when used in reference to an insertion tool, a related instrument, or an implant, are to be taken as relative to the user of the insertion tool. "Proximal" is to be understood as closer to the user and "distal" is to be understood as farther away from the user.

Figure 2:
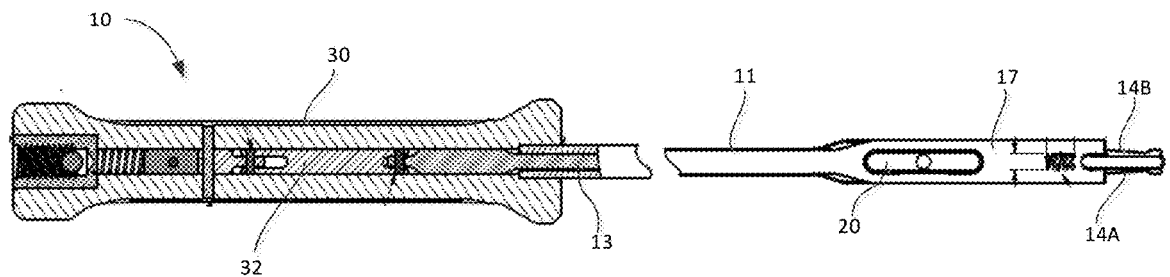
FIG. 2 is a top view of an insertion tool of the system of FIG. 1.
Figure 3:
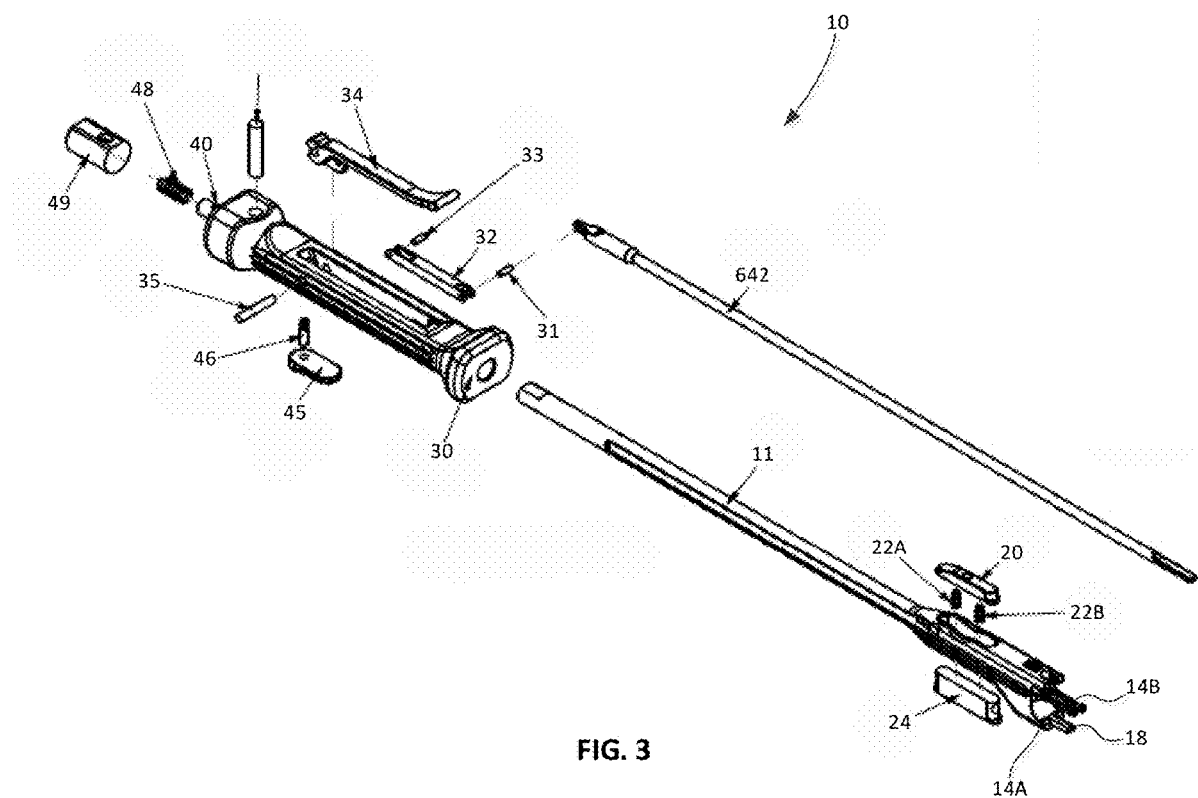
FIG. 3 is an exploded view of the insertion tool of FIG. 2.

In one aspect, the present disclosure relates to an insertion tool structure, as shown in FIGS. 2 and 3. Insertion tool 10 includes a handle 30 and a body in the form of an outer shaft 11.

Figure 37:
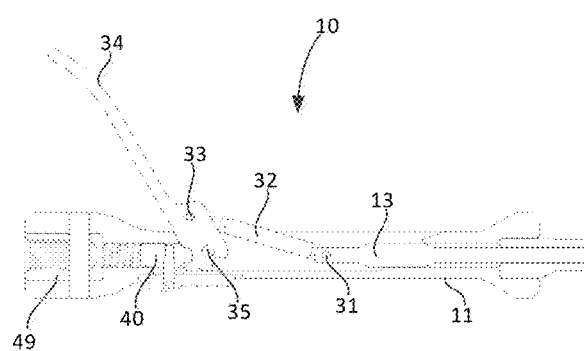
FIGS. 37-38 are partial side and close up views, respectively, of an insertion tool and an intervertebral implant in a step of a method of implantation according to another embodiment of the disclosure.
Figure 39:
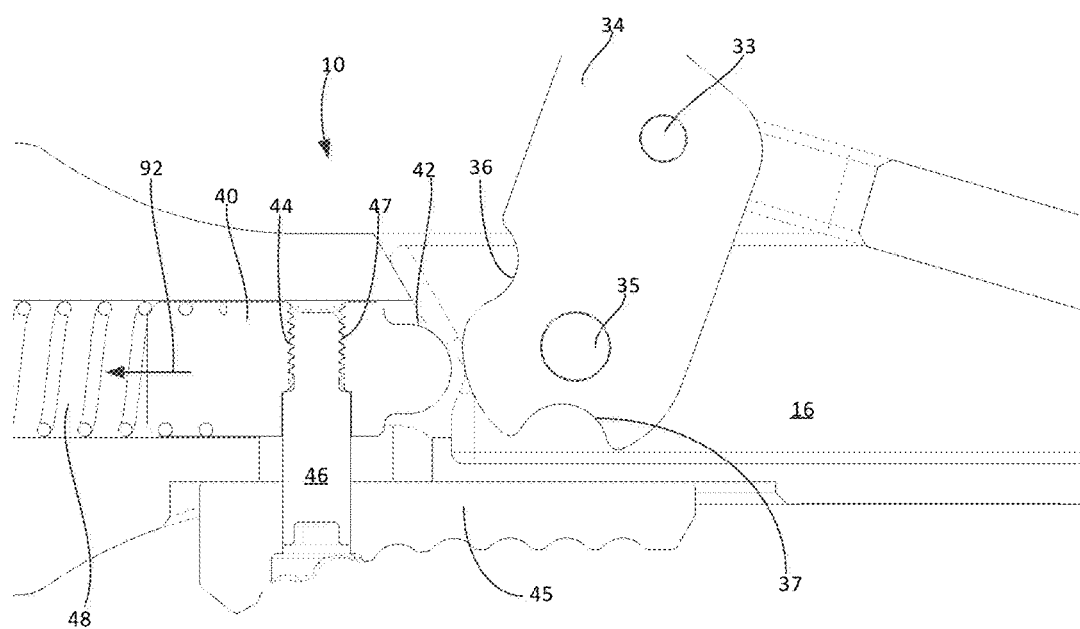
FIG. 39 is a partial close up sectional view of the insertion tool of FIG. 37 in another step of the method.
Figure 40:
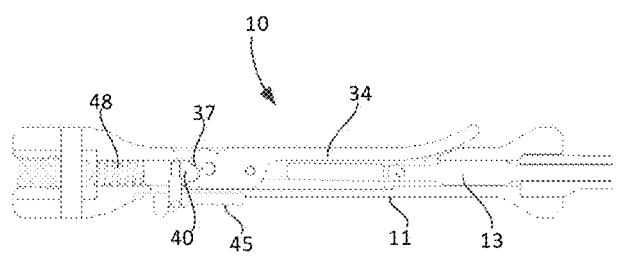
FIGS. 40-42 are various views of the insertion tool and the intervertebral implant of FIG. 37 in another step of the method.

Insertion tool 10 includes a variety of features and components, as shown in the exploded view of FIG. 3. Beginning with handle 30, an opening that is continuous with enclosed passage 16 is included within the handle for disposal of an actuation mechanism. The actuation mechanism is connected to an inner shaft 13 disposed in outer shaft 11 and is described in greater detail below. The opening within the handle is enclosed in part, as shown, for example, in FIGS. 37 and 39. The actuation mechanism includes a lever arm 34 and an internal link 32 connected to one another via pin 33. Lever arm 34 is connected to handle 30 via pin 35. Through the pin connection, lever arm 34 is pivotable about an axis through pin 35 as shown in FIGS. 37, 39 and 40 and described in greater detail below. On a bottom surface of handle 30 opposite the lever arm is a lock button 45, which is secured to handle 30 via a pin 46 that is threaded into a corresponding thread 44 in a ball detent 40, disposed internally within the handle. These features are best shown in FIG. 39. Ball detent 40 is disposed within handle 30 such that it lies immediately proximal to an internally disposed portion of lever arm 34, again, shown in FIG. 39. Proximal to ball detent 40 is a spring 48 and then an end cap 49 closing the enclosed channel of the handle at an end of insertion tool 10. Through this assembly, ball detent is axially adjustable from a biased position abutting the lever arm to a retracted position, with spring compressed, that is spaced apart from the lever arm. Through operative connection of detent 40 with lock button 45, lock button 45 is actuatable to retract detent 40.

Figure 42:
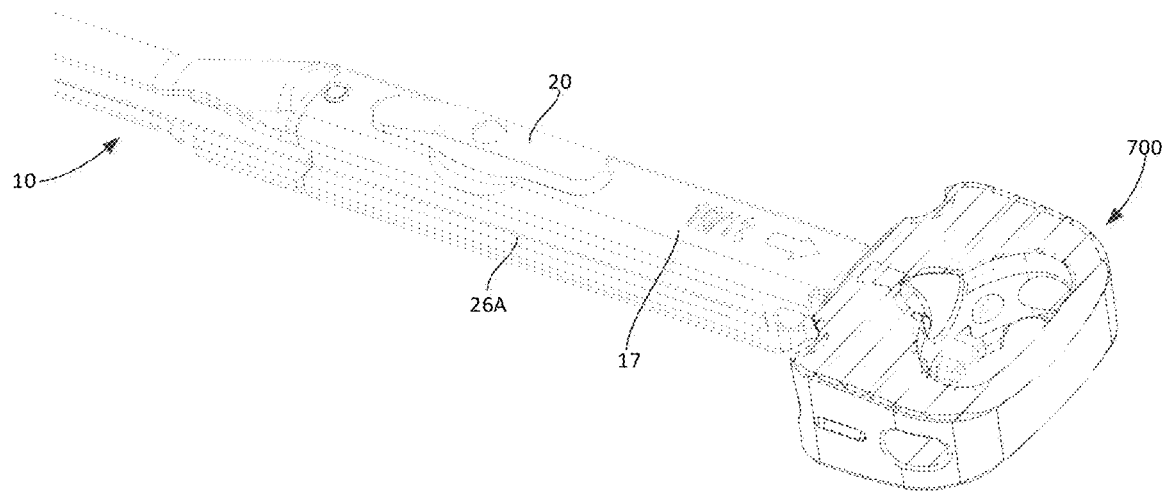
Figure 45:
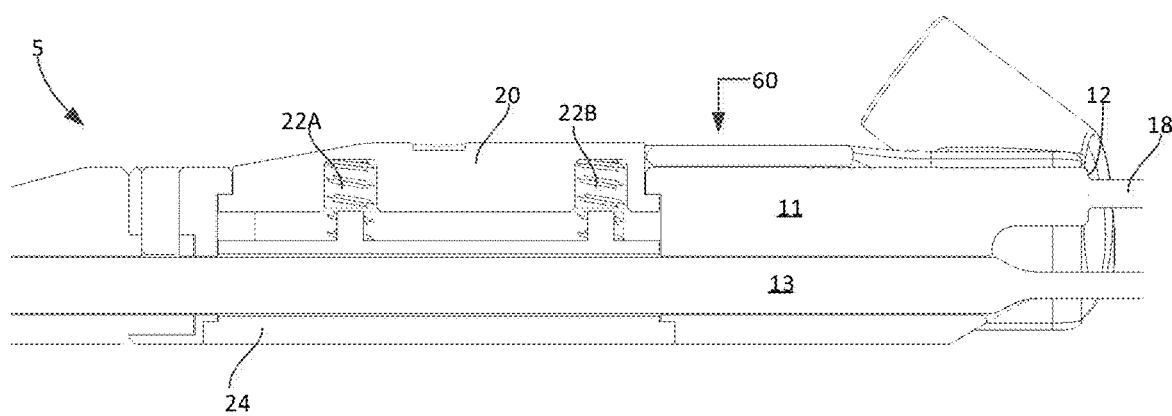

Turning to the leading end of insertion tool 10 that extends from handle 30, outer shaft 11 is axially aligned with handle 30 and is cannulated so that inner shaft 13 is disposed in an enclosed passage 16 therein. Inner shaft 13 disposed in outer shaft 11 is shown in FIG. 37, for example. Inner shaft 13 is operatively connected to lever arm via pin 31, which connects inner shaft 13 with internal link 32. In this manner, the operative connection is such that rotation of lever arm 34 about the axis through pin 35 causes inner shaft 13 to move axially either distally or proximally. At a distal portion 17 of outer shaft 11, outer shaft is of a larger size and includes a button 20 secured thereto via springs 22A-B underneath. In some examples, as shown in FIGS. 3 and 45, a plug 24 is positioned on an opposite side of springs 22A-B relative to button 20 to fully enclose the springs. Without load applied to button 20, button 20 is biased in a raised position relative to a surface of outer shaft 11, as shown in FIG. 42, for example. However, button 20 may be depressed with the application of forces thereon, thereby compressing springs 22A-B. Distal portion 17 of outer shaft 11 also includes a pair of opposing lateral sides, each having an engagement feature in the form of a longitudinally extending slot 26A, 26B therein. As described in greater detail below, these slots are sized for the disposal of a drill guide 60 therein.

Figure 4:
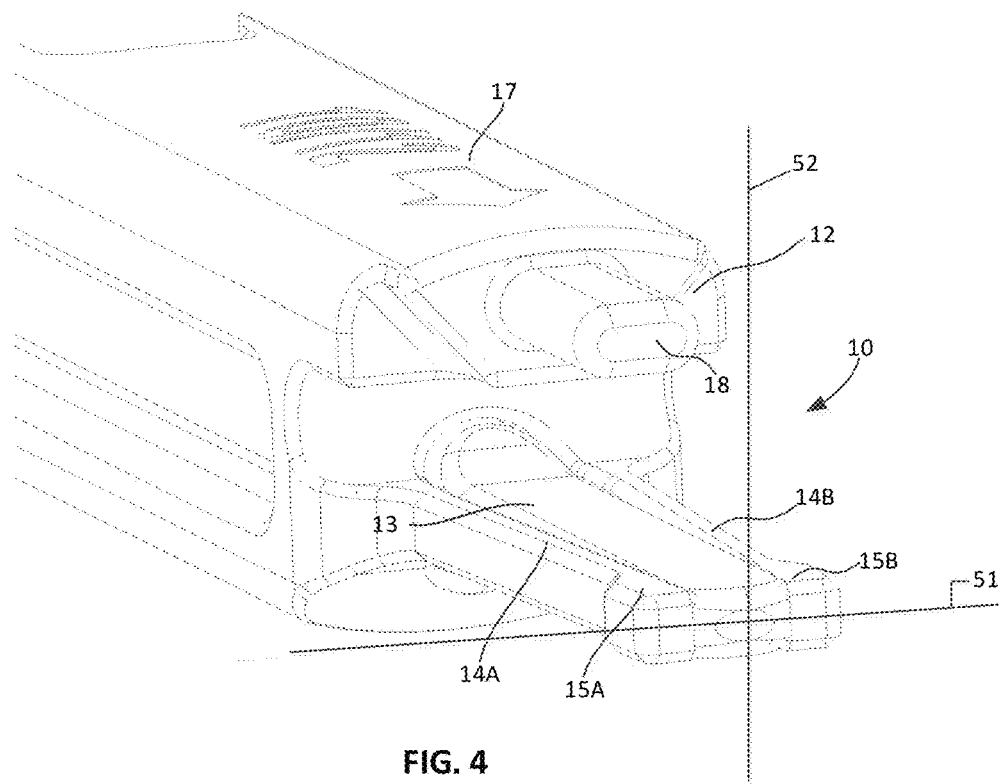
FIGS. 4 and 5 are close up partial views of a distal end of the insertion tool of FIG. 2.
Figure 5:
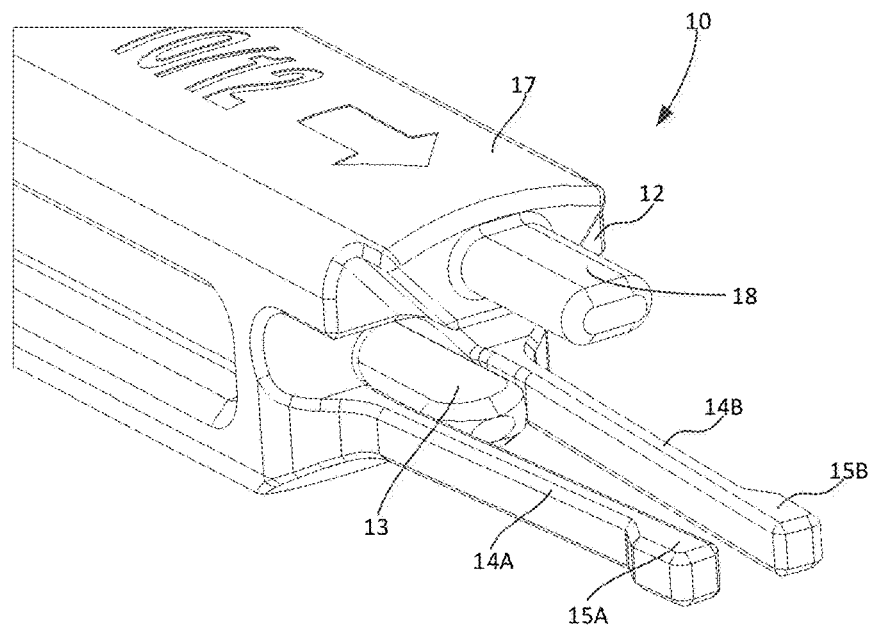

Outer shaft 11 extends to a distal end 12, which is also the end of distal portion 17. From distal end 12, as shown in FIGS. 4 and 5, a pair of arms 14A, 14B that mirror one another extend longitudinally. Arms 14A, 14B are positioned on insertion tool 10 such that enclosed passageway 16 is located immediately in between each arm 14A, 14B. Thus, in the event that inner shaft 13 is advanced distal to distal end 12, inner shaft 13 contacts inside faces of arms 14A, 14B. Each arm 14A, 14B extends to a free end remote from distal end 12 and has a generally uniform shape over most of its length. As shown in FIGS. 4 and 5, each arm has a protrusion 15A, 15B at a respective free end. The protrusions face laterally outward such that surfaces of each arm that face the other arm do not have the protrusion feature. Each arm 14A, 14B is biased slightly inward so that any increase in the distance separating the arms is only preserved while force is applied. Otherwise, the arms return to their biased, or neutral, position.

Offset from a first center axis 51 across the free ends of each arm is a pin 18. As shown in FIGS. 4 and 5, pin 18 also extends from distal end 12 of outer shaft 11. A free end of pin 18 is closer to distal end 12 than the free ends of respective arms 14A, 14B. Pin 18 has a generally uniform and nearly rectangular cross-section over its length although variations in its shape are contemplated to suit a corresponding opening in an implant to be engaged by the insertion tool. Pin 18 is centered on a second center axis 52 along a depth of outer shaft 11. Further, arms 14A, 14B are symmetrical about center axis 52. As shown in FIG. 4, although a combination of the arms and pin are symmetrical about center axis 52, such combination is not symmetrical about an axis perpendicular to center axis 52, such as center axis 51. Indeed, there is no counterpart to pin 18 extending from distal end of insertion tool 10. In this manner, insertion tool 10 has engagement features that are positioned for directional or one-way engagement with an implant.

The insertion tool may be varied in many ways. For example, the insertion tool may be various sizes to accommodate different sizes of implants. Indeed, it is contemplated that the insertion tool may have a size of 10/12, 14/16, 18/20 or 22/24 mm. Each of these sizes may accommodate attachment to at least two different implant heights. In other examples, the pin may be adjacent to an upper surface of the insertion tool instead of being adjacent to a bottom surface, while the arms remain at the same depth on the body of the insertion tool. This may be desirable where the implants intended to be used are smaller. In other examples, four or more engagement features may be used. For example, there may be four prongs and a single pin where each of the four prongs is insertable into a single opening in an implant or into two separate, parallel openings.

Figure 6:
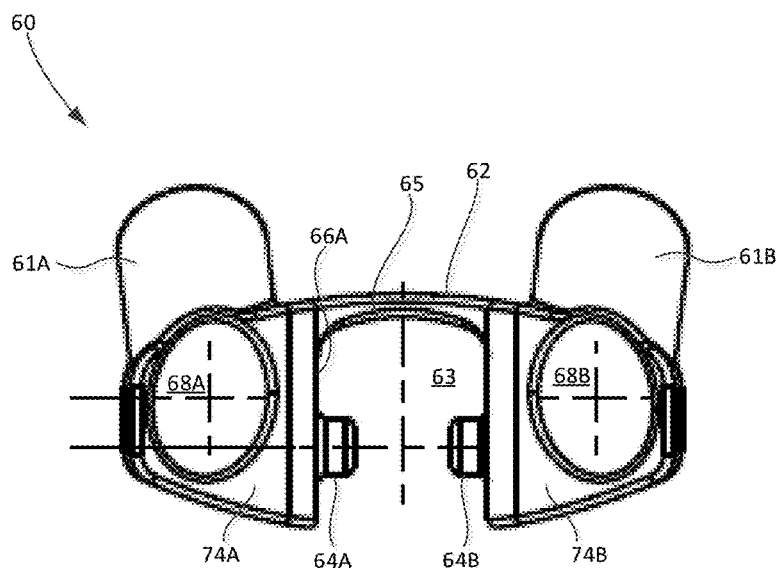
FIGS. 6-8 are various views of a drill guide of the system of FIG. 1.
Figure 7:
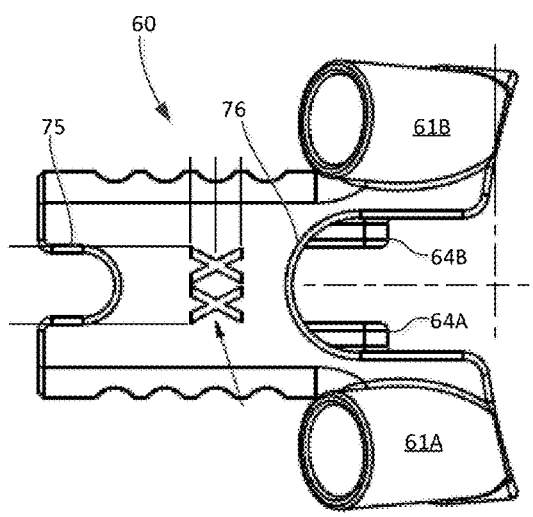
Figure 8:
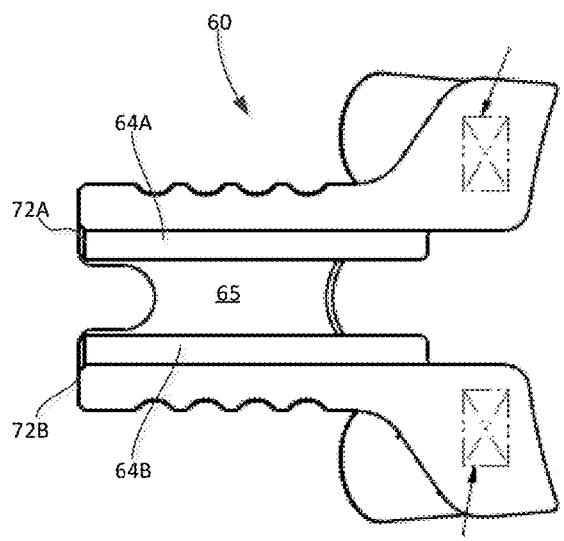

In another aspect, the present disclosure relates to a drill guide. One embodiment of drill guide 60 is shown in FIGS. 6-8. Drill guide 60 includes a central body 62 with a pair of bores 61A, 61B positioned on lateral sides of central body 62. Each bore 61A, 61B includes an opening 68A, 68B, respectively, sized to dispose a driver tool for the fastener therethrough. As shown in each of FIGS. 6-8, the bores are oriented so that an axis through each bore is angled toward a centerline of the drill guide in a direction toward the leading end. A leading end of each bore terminates on a leading end face 74A, 74B of drill guide 60. At an end opposite leading end, central body includes trailing end faces 72A, 72B. As shown in FIGS. 7 and 8, the trailing end faces are separated by an inwardly recessed edge 75. Edge 75 defines an open space over central body 62 sized to allow an end of button 20 to fit within the open space when drill guide 60 is in a secured position with respect to insertion tool 10, described in greater detail in the methods of use of the disclosure.

As shown in FIG. 6, central body 62 includes a central channel 63 along its length, extending from trailing end faces 72A-B to leading end faces 74A-B. Dimensions of channel 63 are defined by side surfaces 66A, 66B and bridging surface 65. Side surfaces 66A-B are generally planar to match an outer surface of outer shaft 11 and, similarly, bridging surface 65 has a slight arcuate shape to match an upper surface of outer shaft 11. Of course, in variations where a shape of outer shaft 11 is different from that shown, a shape of the channel may vary accordingly to match such shape. Protruding from each side surface 66A, 66B are longitudinally extending engagement features in the form of rails 64A, 64B. The rails extend over a portion of the length of the channel and are positioned away from upper and lower ends of the side surfaces, as shown in FIGS. 6 and 8. Alternatively, the rails may extend over a greater or lesser portion of the length of the drill guide. Each rail has a generally rectangular sectional shape with beveled corners, the size and shape of each rail tailored for engagement with a corresponding slot 26A, 26B on a side surface of the outer shaft 11. In this manner, the shape of the rails, and indeed the slots, may vary from that described and shown. Further, the rail and slot combination may be substituted with other complementary engagement features. More detail regarding the function of the rails is provided in the description of the method of using the drill guide elsewhere in the application.

The drill guide may be varied in many ways. For example, as with the insertion tool, the drill guide may be sized for particular implant sizes. Because the drill guide is easily attached to the insertion tool, described in detail in the methods of the disclosure, these size options render it much easier for the user to obtain instrumentation of a particular size that is suitable for a surgery without requiring multiple standalone instruments that have the particular dimensions necessary. In other examples, the rail feature on the drill guide may be substituted with another engagement feature. For instance, the side surface may have a longitudinally extending slot to receive a rail on the insertion tool. A shape of the rail and slot counterpart may also vary.

In another aspect, the present disclosure relates to an intervertebral implant. The intervertebral implant may be adapted for use in an anterior lumbar interbody fusion (ALIF) procedure. It may be used as an interbody with no fasteners or as a standalone device with fasteners.

Figure 9:
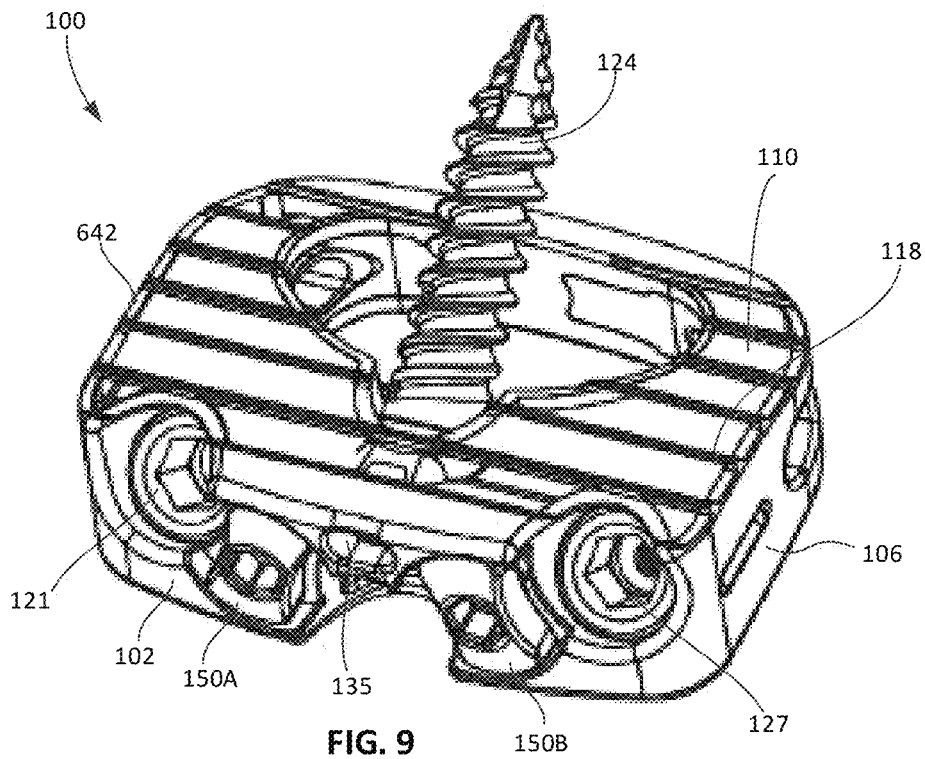
FIGS. 9 and 10 are bottom and top perspective views, respectively, of an intervertebral implant according to one embodiment of the disclosure.
Figure 10:
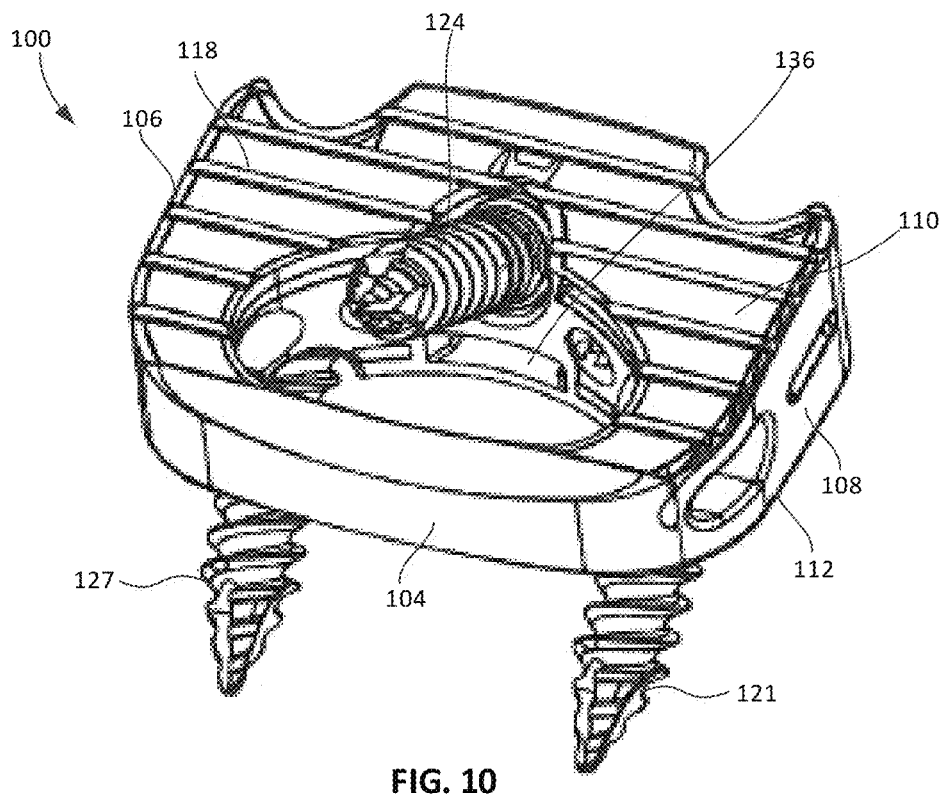

One embodiment of intervertebral implant 100 is shown in FIGS. 9-13. In FIGS. 9 and 10, an overall view of the implant is shown including superior surface 110, lateral side surfaces 106, 108, anterior surface 102 and posterior surface 104. Through superior surface 110 to an inferior surface 112 is a graft window 116. Each of superior surface 110 and inferior surface 112 include fins 118. And, superior and inferior surfaces 110, 112 taper toward one another from the anterior side to the posterior side such that the implant is narrower at the posterior side. In some embodiments, a body of implant 100 is monolithic.

Figure 11:
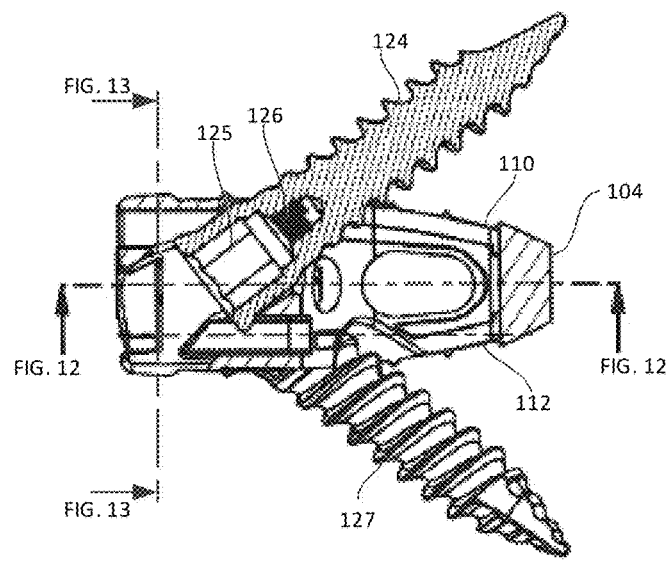
FIGS. 11-13 are various sectional views of the intervertebral implant of FIG. 8.

Implant 100 includes a series of openings for disposal of fasteners and locking elements. Through anterior surface 102 are three openings 131, 134, 137 at approximately equal spacing with respect to one another. Openings 131, 137 are located on opposite sides of the implant and are axially aligned in the same manner such that the openings extend from the anterior surface to the inferior surface. Opening 134, positioned mid-way in between openings 131, 137, extends from the anterior surface to a combination of the superior surface and an interior surface within the graft window, best shown in FIG. 10. In this manner, an alignment of opening 134 is transverse to an alignment of each of openings 131, 137. Each opening has a linear alignment so that fasteners are disposable therein. Fasteners 121, 124, 127 are disposed in openings 131, 134, 137, respectively. Each fastener includes engagement features to drive the fastener into place. For example, as shown in FIG. 11, fastener 124 includes a hex drive 125 and an internal thread 126. Of course, these features may vary to suit the use of drivers with other tip shapes. Openings 131, 134, 137 have rounded surfaces on the anterior side of the implant so that each fastener may be angulated up to five degrees from a nominal alignment, thereby providing flexibility for the user.

Figure 13:
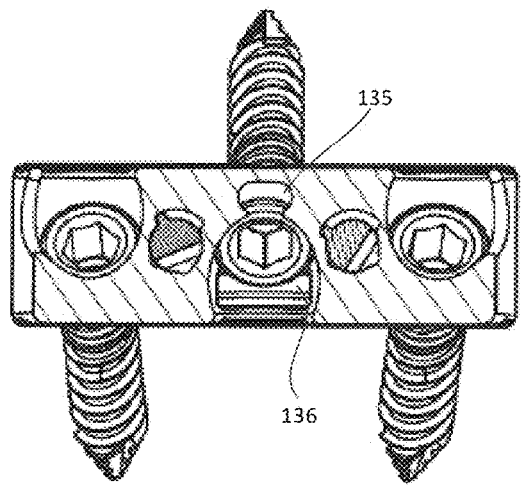

Within opening 134 is an additional opening 136 extending from within opening 134 to an internal surface of the implant, as shown in FIGS. 10 and 13. Opening 136 is sized so that arms of an insertion tool are positionable therethrough when slightly compressed. Also centered on anterior face but separate from openings 134, 136 is opening 135. Opening 135 is an oblong shape as shown in FIGS. 9 and 13 and extends partially into implant 100. Opening 135 is sized so that a pin of an insertion tool is disposable therein. In an alternative configuration, the opening for the pin may extend from the anterior surface through to the interior surface of the implant defining the graft window. Additionally, the opening for the pin may begin from within opening 134 or separately from outside of it. The combination of openings 135, 136 defines an asymmetrical surface on implant 100 through the offset position of opening 135. Thus, the implant is designed so that the insertion tool may only be inserted into the implant in one orientation. In this manner, the engagement between the insertion tool and implant is directional. If the insertion tool is upside down, pin 18 will encounter anterior surface 102 upon contact with implant and will prevent securement of the insertion tool with the implant. Further to the directional engagement feature, one advantage of the implant is that once the implant is secured to the insertion tool, the implant on the end of the tool may be inserted into an intervertebral space either with the superior surface of the implant or the inferior surface of the implant facing upward. In either orientation, the same functionality is provided. With regard to securement between insertion tool 10 shown in FIGS. 2-5 and an implant, it should be appreciated that implant 700 is shaped particularly for engagement by arms 14A, 14B and pin 18 of insertion tool 10. Implant 700 is described in greater detail below.

Figure 12:
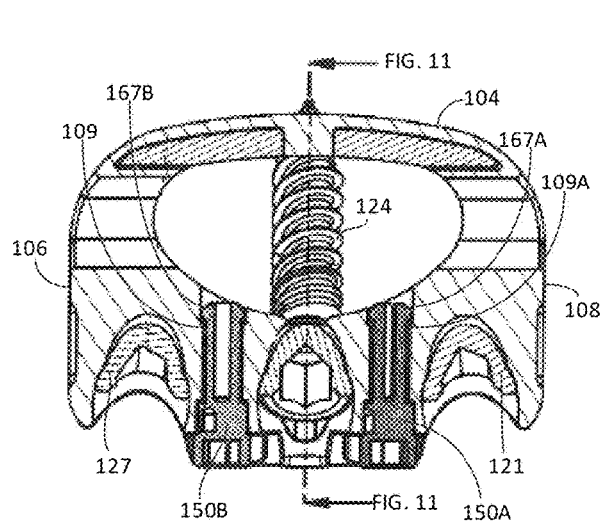
Figure 14:
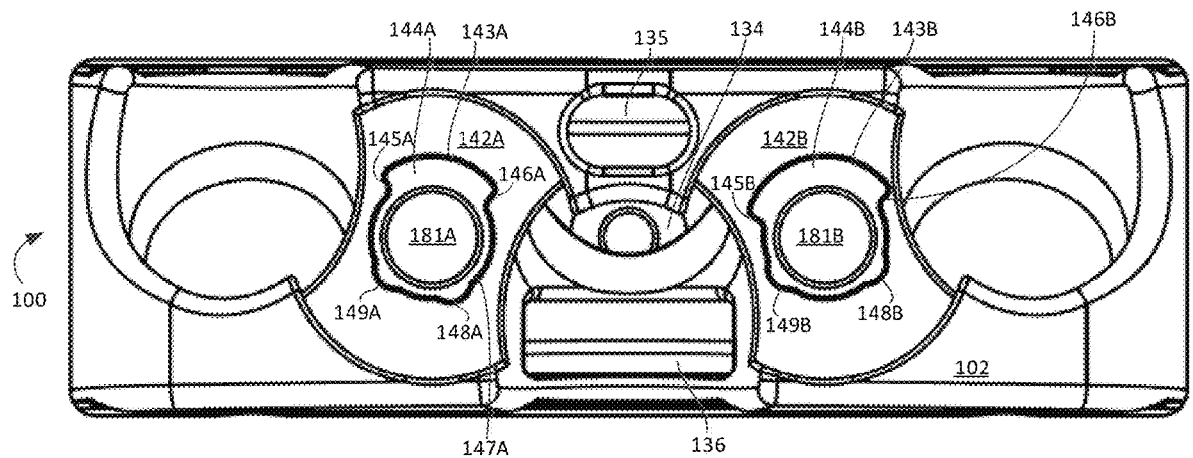
FIG. 14 is a sectional view of the intervertebral implant of FIG. 9 without locking elements and fasteners.

In between openings 131, 134 is another opening 181A shown in FIGS. 12 and 14 that extends from anterior surface 102 to an interior surface of graft window 116. Opening includes a lip 109A near the graft window end of the opening. A second opening 181B of the same shape is located between openings 134, 137. Disposed within each of these openings is a locking element 150A, 150B. Each locking element is sized to fit fully and securely within the designated openings within the implant, as shown for example, in FIG. 12. The details of the locking elements will now be described. For clarity, only the structure of locking element 150A is described, but it should be appreciated that locking element 150B shares the same structural features.

Figure 15:
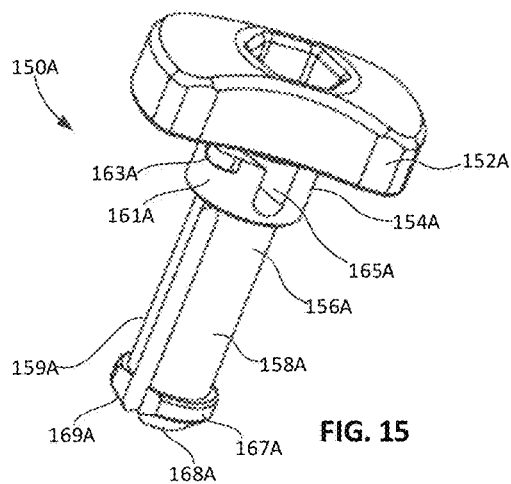
FIGS. 15-18 are various views of a locking element of the intervertebral implant of FIG. 8.
Figure 16:
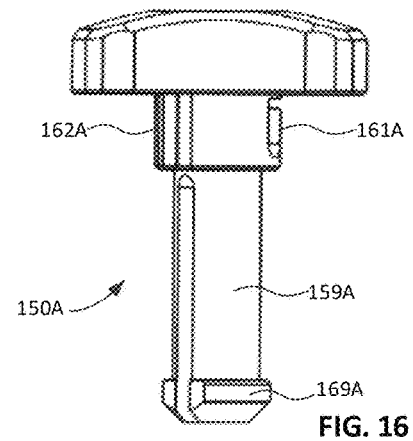
Figure 17:
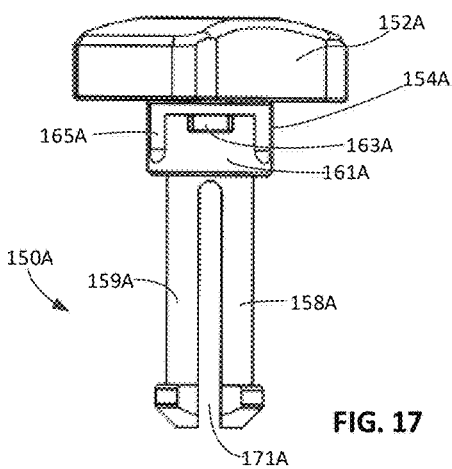
Figure 18:
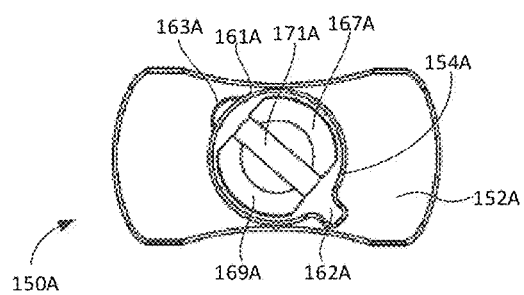

As shown in FIGS. 15-18, locking element 150A includes a head 152A, a flexible base 154A that abuts head 152A, and a shaft 156A that extends from base 154A. Head 152A is oblong and has a width greater than a diameter of both base 154A and shaft 156A. Base 154A is cylindrical with a space 165A formed therein. Space 165A is L-shaped and divides base 154A into a main portion and a flexible bar 161A. Flexible bar 161A is a cantilever that extends from an end of base 154A that abuts shaft 156A to a free end facing head 152A, as shown in FIGS. 16 and 18. The exact shape of space 165A may vary provided that the flexible bar extends to a free end. The geometry of flexible bar 161A and its space from the main portion of base 154A causes flexible bar 161A to deform when subject to a threshold load. In a neutral position without loads applied, an inside surface of flexible bar 161A is generally parallel to an inside surface on the main portion of the locking element, as shown in FIG. 15. Extending outwardly from a rounded surface of flexible bar 161A is protrusion 163A positioned at the free end of flexible bar 161A. Also on base 154A is ridge 162A that protrudes from an outer surface of base 154A. As shown in FIG. 18, ridge 162A is directly opposite protrusion 163A and, as shown in FIG. 16, ridge 162A extends over a length of base 154A traversing a distance between head 152A and shaft 156A.

Turning to shaft 156A, the shaft includes two prongs 158A, 159A that are separated by slit 171A. Each prong is approximately equal in size and includes a radial ridge 167A, 169A that defines at wider portion near a distal tip of locking element 150A, along with a tapered distal end 168A. When disposed in implant 100, radial ridge 167A sits above lip 109A to hold locking element 150A toward anterior side in an axial direction. Each prong 158A, 159A is biased in the manner shown so that each one is pushed closer to the other to place locking element 150A through opening 181A. Thus, when in position over lip 109A, an inward force on the prongs is required to pull the locking element anteriorly. Between base 154A and radial ridge 167A, shaft 156A is generally cylindrical with the exception of the slit between prongs 158A, 159A.

Returning to the main structure of intervertebral implant 100, from an anterior side of implant 100 through anterior surface 102 are geometric features surrounding openings for the locking elements that support the disposal, adjustability and securement of the locking elements in the implant. To describe these features reference is made to FIG. 14 and opening 181A that receives locking element 150A. However, again, it should be appreciated that opening 181B has the same features for receipt of locking element 150B.

Surrounding opening 181A are a pair of stepped surfaces that are progressively closer to anterior surface 102. Immediately surrounding opening 181A is second recessed surface 144A and surrounding the second recessed surface is first recessed surface 142A.

Second recessed surface 144A has an inner edge defined by opening 181A while its outer edge is a perimeter that abuts a step to first recessed surface 142A. In particular, the perimeter is divided into two segments separated by a first location 145A and a second location 146A. A first segment 147A of the edge that extends between the first location and the second location is curved, has a first radius along its length and spans more than half of a circumferential distance around opening 181A. Along the length of first segment 147A, the edge deviates from the first radius at two, spaced locations 148A, 149A. At each of these locations, the edge is recessed away from opening 181A, as shown in FIG. 14. Although the edge has a concave rounded edge at each recess 148A, 149A, it is contemplated that such shape may be varied to accommodate matching surface features on the locking element used with implant 100. A second segment 143A extending between ends of the first segment at first and second locations 145A, 146A is curved and has a second radius along its length. As shown in FIG. 14, the second radius is greater than the first radius.

An inside edge of first recessed surface 142A abuts the edge of second recessed surface, again shown in FIG. 14. An outer edge of first recessed surface has two separate segments opposed from one another, each having the same radius and abutting a step to anterior surface 102. The segments are separated by openings 131, 134 for the fasteners in the implant. Thus, the edges that bridge each of the opposed segments are defined by the radius of openings 131, 134. The recessed surfaces are dimensioned and define a volume in the implant such that portions of the locking element are disposable therein. In particular, at least part of base 154A is disposable in a volume defined by second recessed surface 144A and at least part of head 152A is disposable in a volume defined by first recessed surface 142A. More detail on the interaction between the locking element and the implant surfaces is provided in the description of the method.

Figure 19A:
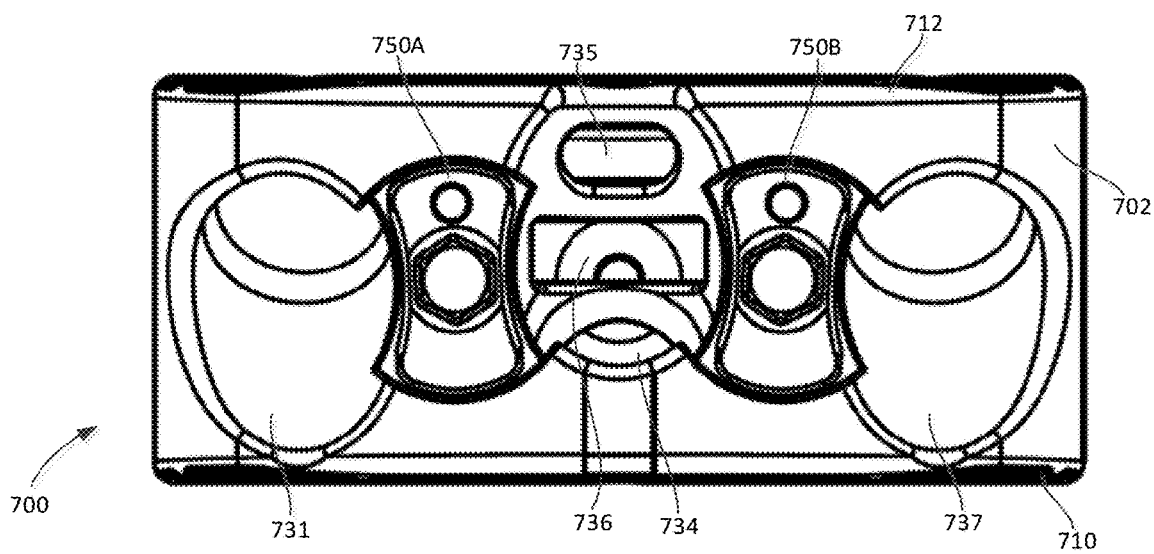
FIGS. 19A-19B are side and perspective views of an implant according to another embodiment of the disclosure.
Figure 19B:
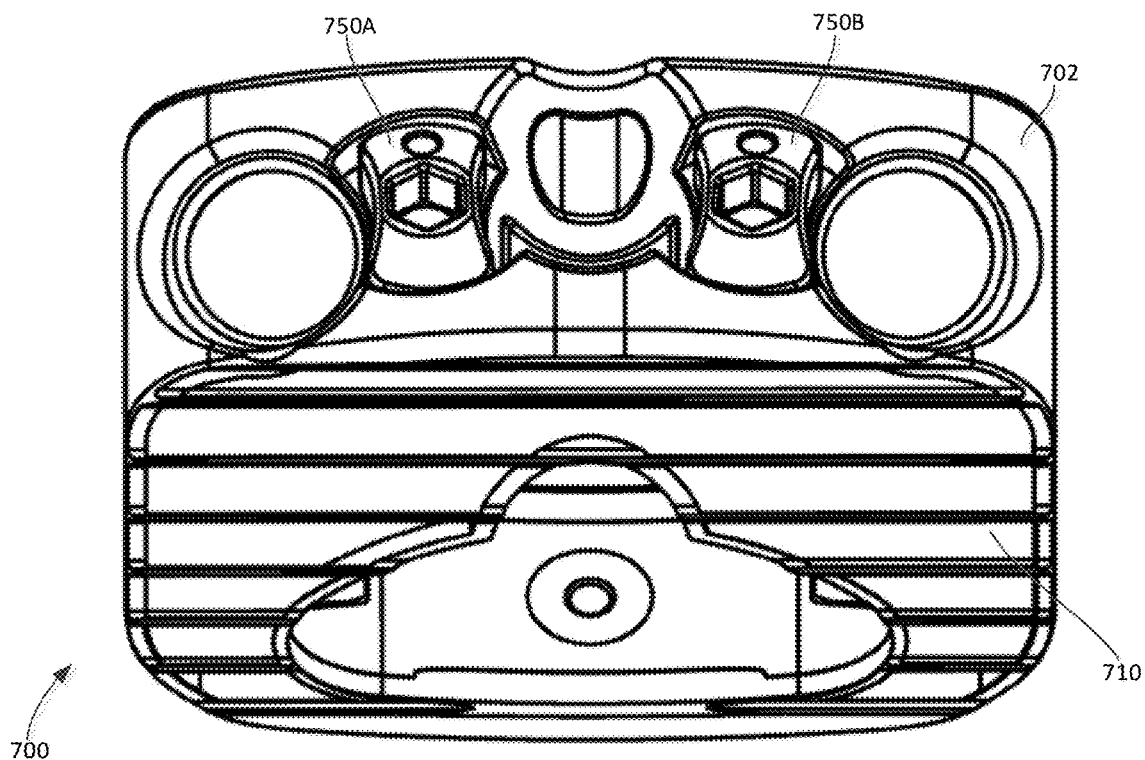

Another embodiment of an intervertebral implant is shown in FIGS. 19A-B. Unless otherwise stated, like reference numerals refer to like elements of above-described intervertebral implant 100, but within the 700-series of numbers. Implant 700 includes locking elements 750A, 750B that are the same as locking elements 150A, 150B. Further, implant 700 surface features beneath the locking elements (not shown) are the same as those described for implant 100, thereby providing the same structure to move locking elements between unlocked and locked positions. However, in contrast to implant 100, opening 735 that is sized for disposal of pin 18 therein is adjacent to inferior surface 712, unlike implant 100. In this manner, openings 735, 736 are sized and positioned in implant 700 for disposal and engagement by pin 18 and arms 14A, 14B of insertion tool 10, respectively, as the pin is positioned to match the opening closest to the inferior surface of the implant. The complementary nature of the features of insertion tool 10 and implant 700 is shown through a comparison of FIG. 4 and FIG. 19A, for example. In FIGS. 19A-B, opening 735 is separate from opening 734. However, in alternatives such as those noted above, the openings may also commence from a common opening in the implant.

In another embodiment, implant 200 is shown in FIG. 20. Unless otherwise stated, like reference numerals refer to like elements of above-described intervertebral implant 100, but within the 200-series of numbers. Anterior surface 202 includes a recessed surface (not shown) between openings 231, 234 and 234, 237, respectively. Each recess is stepped below anterior surface 202. With reference to locking element 250A as representative, and the recessed surface associated with locking element 250A, the recessed surface has an arcuate perimeter with a first radius that measures about the same as a long dimension of a head 252A of locking element 250A. Further, one segment of the edge of the recessed surface includes two separate inward bulge features that appear as bumps on the arcuate path of the recessed surface edge. These bulges are sized to fit a pair of recessed grooves 272A, 273A on one side of head 252A of locking element 250A, as shown in FIG. 20. The above described structure allows locking element 250A to move between two positions, one where both grooves 272A, 273A are locked with respective bulges in the recessed surface and another where one groove is locked. In FIG. 20, locking element 250B is shown with one groove 273B locked to a bulge in the recess on the surface of the implant. In either position, the locking element is rotationally fixed relative to the implant.

In yet another embodiment, implant 300 is shown in FIGS. 21, 22A and 22B. Unless otherwise stated, like reference numerals refer to like elements of above-described intervertebral implant 100, but within the 300-series of numbers. Implant 300 includes locking elements 350A, 350B. With reference to locking element 350A as representative, locking element 350A includes head 352A having an open channel 365A on one side, as shown in FIGS. 21 and 22A. The open channel separates a main body of the head from flexible bar 361A, which extends from the main body of head 352A to a free end. Adjacent the free end of flexible bar 361A is protrusion 363A that protrudes outward away from a remainder of head 352A. Flexible bar 361A is shaped and positioned so that when subject to loads, flexible bar 361A deforms to move closer to the main body of head 352A. Shaft 356A abuts head 352A, as shown in FIG. 22A. An inner protrusion 362A extends radially from shaft 356A in a direction facing flexible bar 361A, again shown in FIG. 22A. When locking element 350A is disposed in implant 300, inner protrusion 362A fits within a corresponding recess within implant 300 in a manner similar to ridge 162A of locking element 150A. And, although flexible bar 361A is located on head 350A, protrusion 363A locks into either groove of grooves 348A, 349A that define a recessed surface on anterior surface 302 in a manner similar to protrusion on flexible bar 161A of locking element 150A locking into either groove 148A, 149A. It should be appreciated that the inner protrusion feature may also be included on locking elements 250A, 250B used with implant 200 to prevent over rotation.

Locking elements 350A, 350B are positioned through corresponding openings in the implant. In particular, and as shown in FIG. 22B, head 352B of locking element 350B is disposed in an open volume below anterior surface 302, while shaft 356B extends through opening 381B. From the open volume to a surface of graft window 316, opening 381B flares outward and becomes wider. In this manner, a risk of back out of locking element is reduced as a minimum amount of force will be required to pull radial ridge 367A in an anterior direction through the opening while it is initially blocked by a surface of opening 381B that becomes narrower closer to anterior surface 302. The opening shown in FIG. 22B and described above may also be included in implant 200.

Figure 23:
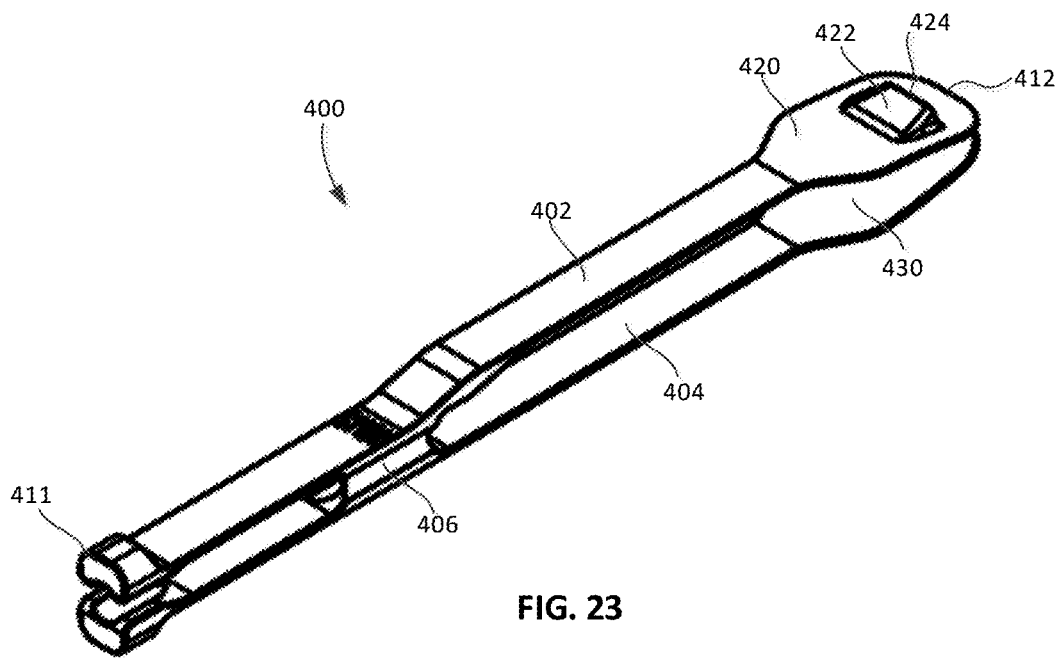
FIGS. 23 and 24 are perspective and side views, respectively, of a graft clip according to another embodiment of the disclosure.
Figure 24:
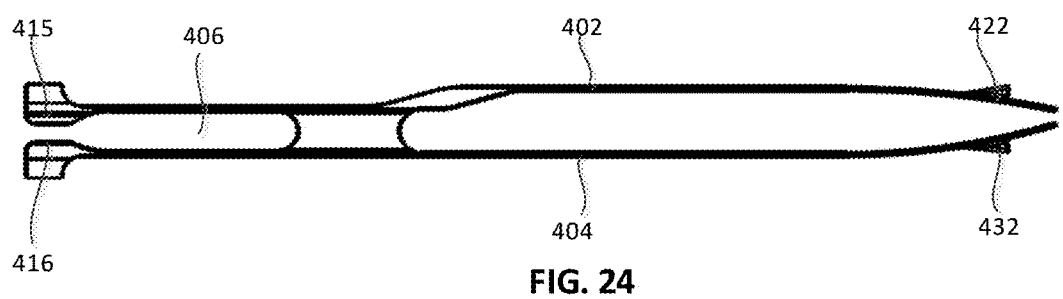

In another aspect, the present disclosure relates to a graft clip. In one embodiment, and as shown in FIGS. 23 and 24, graft clip 400 includes an upper grip arm 402 and a lower grip arm 404 that extend from a proximal end 411 to a distal end 412. Grip arms 402, 404 are joined through connective element 406, which joins one side of the respective grip arms. In this manner, a space between grip arms 402, 404 is entirely open on one side, but is blocked by connective element 406 on the side shown in FIG. 23. An internal space between upper grip arm 402 and lower grip arm 404 is sized to accommodate disposal of outer shaft 11 therein. Further, inner surfaces 415, 416 on respective grip arms at proximal end 411 are rounded and sized for snap in engagement of outer shaft 11 so that outer shaft 11 is securable to graft clip 400.

Each grip arm has a similar shape, though in the variant in the figures, upper grip arm 402 includes an angled portion along its length such that a space between the grip arms is greater over a portion of the length. Toward the distal end, each arm tapers toward the other, as shown in FIG. 24. Also near distal end 412, each grip arm has a paddle that is wider than a remainder of the arm and includes a stop feature that faces outward away from the opposing arm. Thus, upper grip arm 402 includes upper paddle 420 with upper stop 422. Upper stop 422 protrudes from a surface of upper paddle 420 with an increasing depth toward distal end 412. A maximum depth of upper stop 422 defines a ridge 424. The feature of lower paddle 430 and lower stop 432 for graft clip 400 are the same as those on upper grip arm 402.

Figure 25:
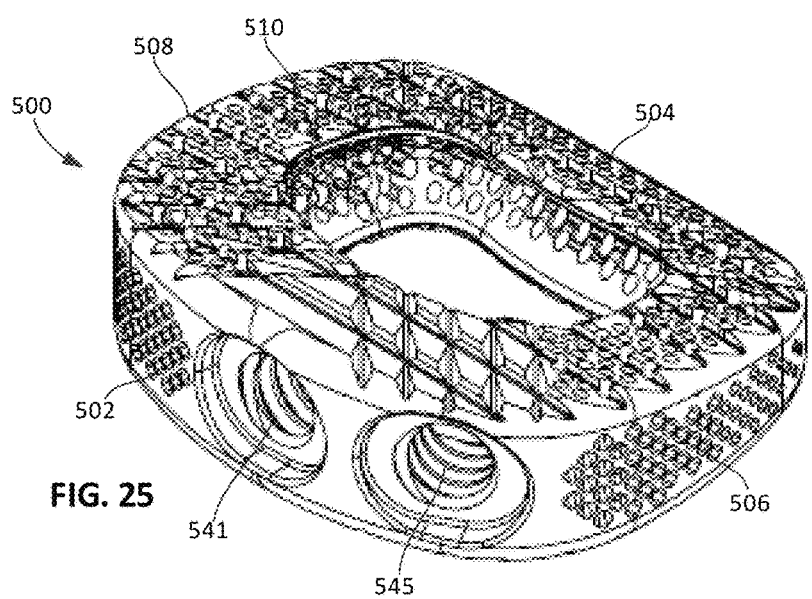
FIGS. 25-30 are various views of an intervertebral implant according to another embodiment of the disclosure.
Figure 26:
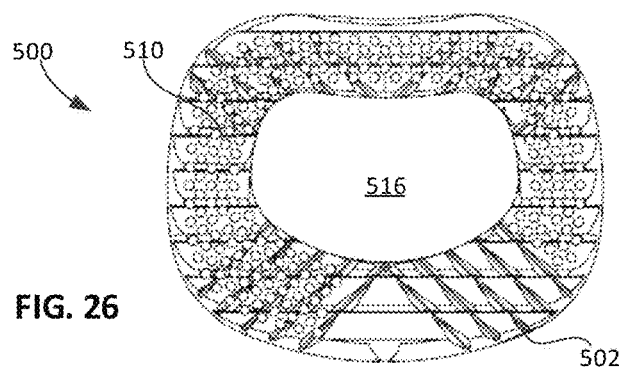
Figure 27:
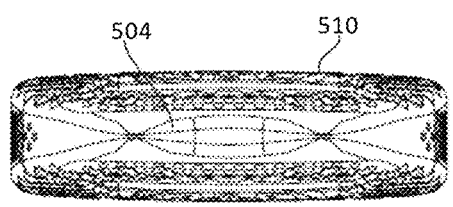
Figure 29:
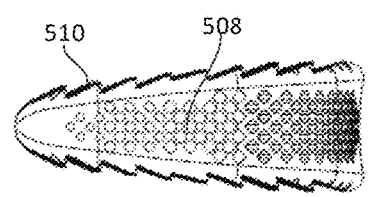
Figure 28:
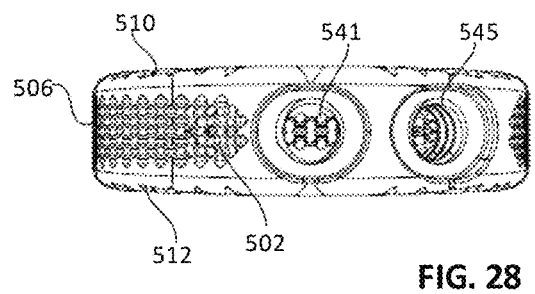
Figure 30:
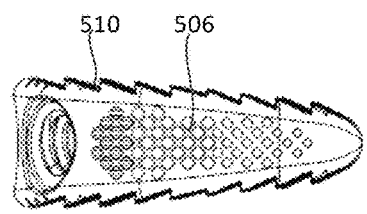
Figure 31:
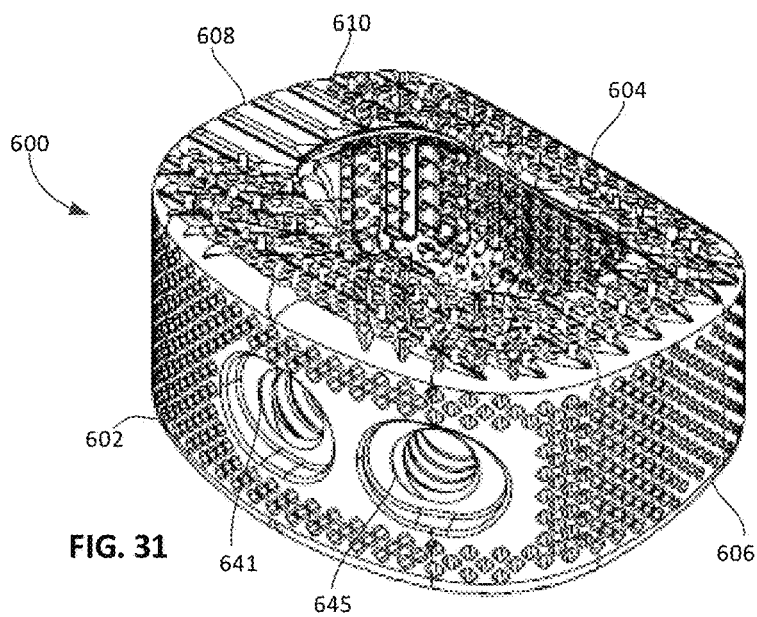
FIGS. 31-36 are various views of an intervertebral implant according to another embodiment of the disclosure.
Figure 32:
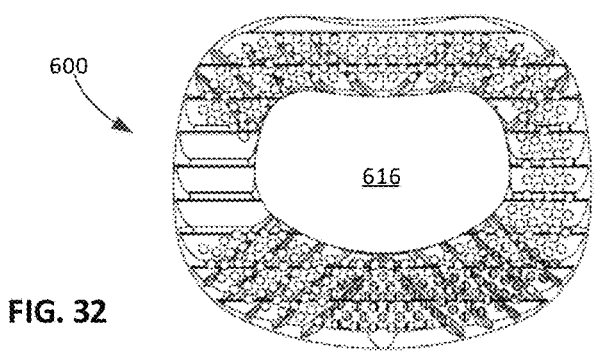
Figure 33:
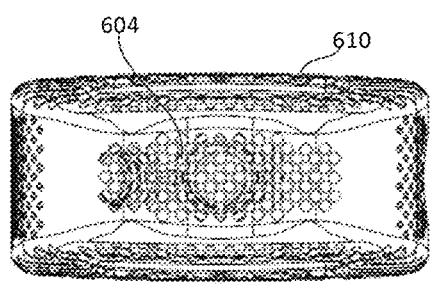
Figure 35:
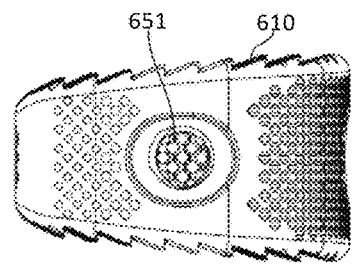
Figure 34:
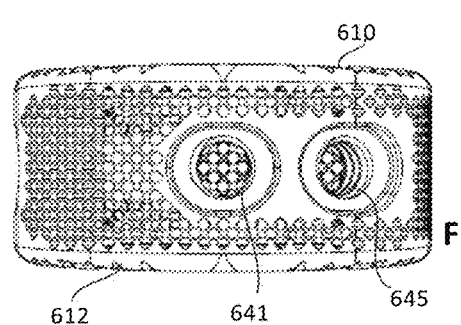
Figure 36:
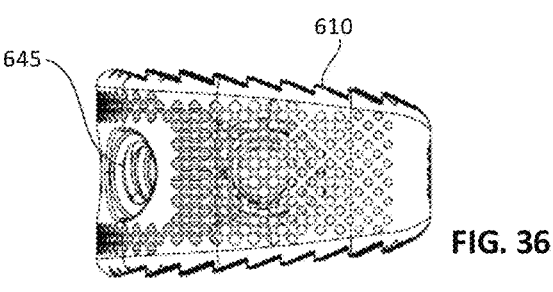

In another aspect, the present disclosure relates to a lordotic intervertebral implant, one embodiment of which is shown in FIGS. 25-30. Unless otherwise stated, like reference numerals refer to like elements of above-described intervertebral implant 100, but within the 500-series of numbers. Surfaces 506, 508, 510, 512 of lordotic intervertebral implant 500 include a distribution of diamond shaped holes that extend through the body to an opposing side. Anterior surface 502 also includes diamond shaped holes through its surface, although only through part of the surface, as shown in FIGS. 25 and 28. These holes give the implant a predetermined degree of porosity. Posterior surface 504 does not include holes, as shown in FIG. 27. In variants, the diamond shaped holes as shown may be substituted with holes having other shapes.

Implant 500 also includes two openings 541, 545, as shown in FIGS. 25 and 28. Opening 541 is aligned with a center axis of implant 500 and extends from anterior surface 502 to an interior surface that borders graft window 516. Opening 145 is aligned at an angle relative to opening 541 and also extends from anterior surface 502 to the interior surface. Opening 545 is positioned such that its exit location on anterior surface is on a lateral side of anterior surface. As depicted, the alignment of opening 545 is less than forty five degrees relative to an alignment of opening 541. However, in variations, the alignment of opening 545 may vary. Each opening 541, 545 is defined by a threaded inner wall. With the availability of these uniquely positioned openings on the anterior surface, implant 500 is insertable into the spine with its lateral sides aligned with an insertion tool when attached via opening 541. Implant 500 is also insertable at an angle relative to an axis of an insertion tool when secured to the tool via opening 545. This provides the user with multiple options for an approach to the spine to place the implant in a desired orientation, which is advantageous where access is limited to certain approaches.

In another embodiment, lordotic intervertebral implant 600 is shown in FIGS. 31-36. Unless otherwise stated, like reference numerals refer to like elements of above-described intervertebral implant 500, but within the 600-series of numbers. Implant 600 is taller than implant 500 and has a greater depth to width ratio. Implant 600 includes holes on all surfaces, including posterior surface 604. Further, in addition to openings 641, 645 positioned in a manner similar to openings in implant 500, implant 600 also includes opening 651, shown in FIG. 35, extending through lateral surface 608 and into a surface that defines graft window 616. Opening 651 allows an insertion tool to be attached from the lateral side of implant 600, thereby providing another option for directing the insertion tool into the intervertebral space. Thus, for example, to place implant 600 in the intervertebral space in a desired orientation, the availability of three openings accessible from three different locations on the implant surface, each at different approach angles, allows the user to direct the implant into the space from at least three different approaches.

In another aspect, the present disclosure relates to a system for implantation of intervertebral implants. In one embodiment, system 5 includes an insertion tool 10 and drill guide 60. In other embodiments, the system may include a combination of any insertion tool and any drill guide contemplated herein. In one embodiment, a system includes an insertion tool and a graft clip.

In another aspect, the instruments and implants contemplated herein may be included as part of a kit. In one embodiment, a kit includes an insertion tool, a drill guide and a graft clip. In some embodiments, a kit includes two or more of any one of the aforementioned instruments. For example, a kit with multiple insertion tools may include insertion tools in any number of sizes including 10/12, 14/16, 18/20 and 22/24 mm. In other embodiments, a kit includes two or more implants. In some examples, the implants may be the same, in others, the implants in the kit may be different or there may be groups of implants within a larger set that are the same. In other embodiments, a kit includes a combination of instruments and implants. Any number of a particular instrument or implant may be included in these variations. It should be appreciated that the above embodiments are illustrative and that any combination of the above embodiments may be used to form a kit.

In some embodiments, a kit includes a combination of instruments and/or implants as described above along with other instruments or other materials used in spinal surgery, such as a screw driver. The kit may be varied in many ways. For example, the various combinations of elements of any contemplated kit may be included in a single package or distributed among multiple packages. In other examples, the kit contemplated herein may be accompanied by an instruction manual on how to perform one or more of the methods of using the contents of the kit.

Figure 38:
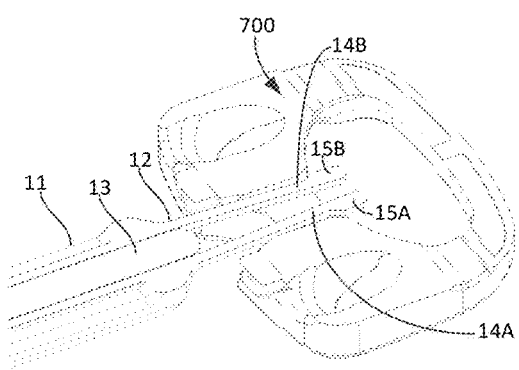

In another aspect, the present disclosure relates to a method of inserting an intervertebral implant into an intervertebral space in a body of a patient. In one embodiment, shown in FIGS. 37-45, insertion tool 10 is advanced into engagement with implant 700, as shown in FIG. 38. In particular, arms 14A, 14B are advanced through opening 134 and pin 18 is advanced through opening 135. Pin 18, when inserted along with arms 14A, 14B, prevents rotation of the insertion tool relative to the implant during use. Pin 18 also prevents forces from acting on arms 14A, 14B. During advancement, the arms flex inward to fit through the opening. Once protrusions 15A, 15B of the respective arms pass through opening 134, the arms snap outward toward their biased position, shown in FIG. 38. During this time, and as shown in FIG. 37, lever arm 34 is positioned such that it is pivoted rearward and inner shaft 13 is in a withdrawn position. Once arms 14A, 14B are in the desired position within implant 700 so that protrusions 15A, 15B hook onto the inner surface of the graft window, the implant is ready to be locked to insertion instrument 10.

Figure 41:
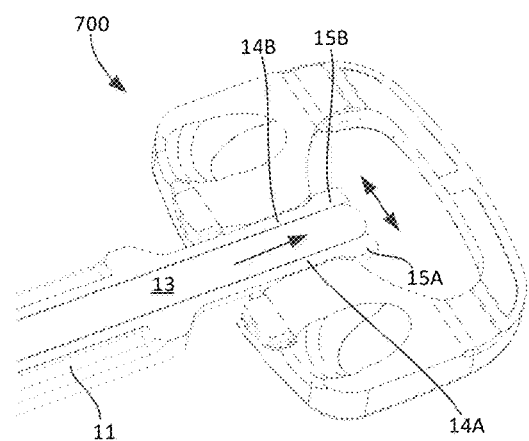

To lock the implant, lever arm 34 is pushed distally, i.e., away from the user, to overcome engagement between first groove 36 and ball detent 40. As lever arm 34 is pivoted in this manner, inner shaft 13 advances axially within the outer shaft until it pushes in between arms 14A, 14B, as shown in FIG. 41. Lever arm 34 is pushed further until second groove 37 engages ball detent 40, locking lever arm 34 to ball detent 40 and causing inner shaft 13 to hold in place between arms 14A, 14B. Although this advancement does not substantially change the position of protrusions 15A, 15B hooked on the inside surface of implant 700, it prevents the arms from collapsing inward due to any forces applied to the insertion tool. In this manner, insertion tool 10 is prevented from accidentally withdrawing from implant 700. A perspective view of implant secured to insertion tool 10 is shown in FIG. 42.

Alternatively, to lock the insertion tool to the implant, lock button 38 is drawn toward the user in the direction indicated by reference numeral 92 in FIG. 39. As the button is drawn, ball detent 40 disengages from second groove 37 in lever arm 34. This allows lever arm 34 to rotate freely. Lever arm 34 is then rotated in a distal direction away from the user as shown in FIG. 40. The button may be used in the same manner at another time to unlock the insertion tool from the implant. On a bottom side of handle 30 adjacent to button 20, a marking may be included to indicate a direction to actuate button in order to unlock the lever arm from the ball detent. For example, the marking may be an arrow beside the word "UNLOCK." Of course, other words or symbols may also be used to provide an indication for operation to the user.

Figure 43:
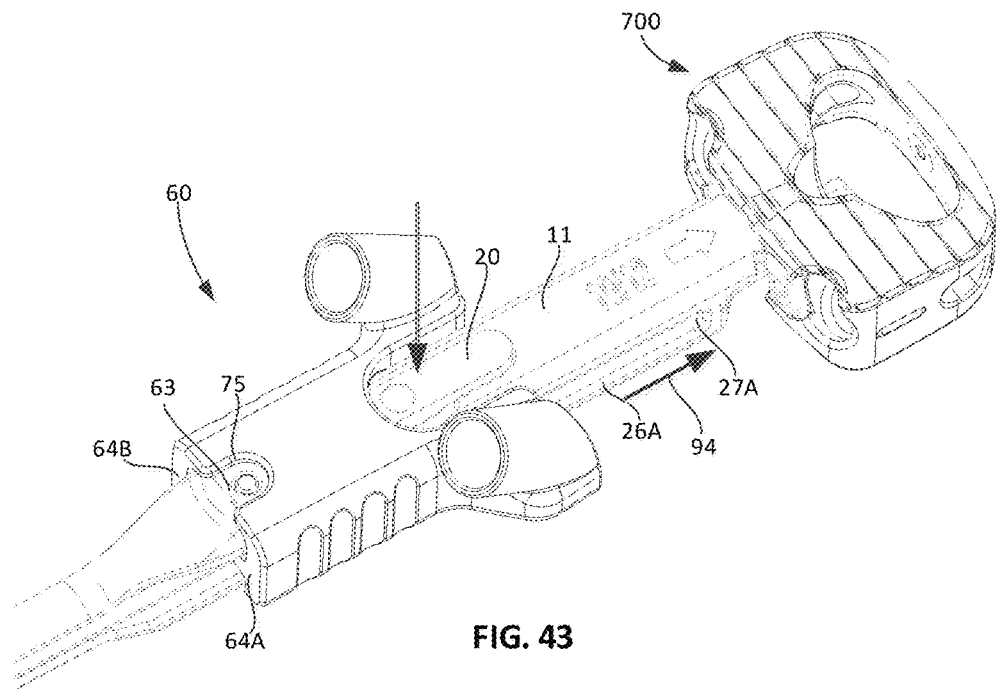
FIG. 43 is a perspective view of the insertion tool of FIG. 37 with a drill guide engaged in another step of the method.
Figure 44:
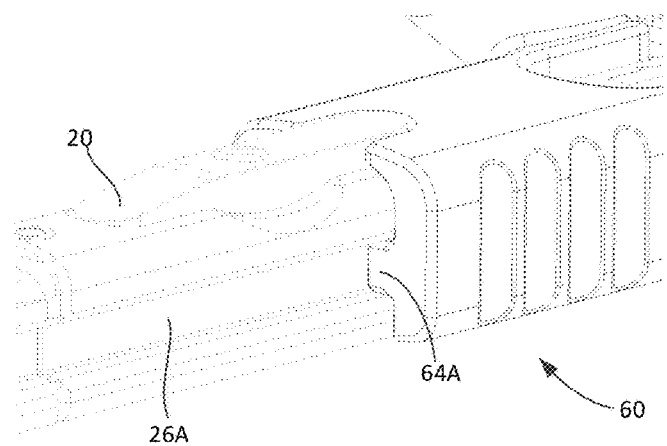
FIGS. 44 and 45 are close up perspective and sectional views, respectively, of the insertion tool and the drill guide of FIG. 42 according to another step of the method.

In a subsequent step of the method, drill guide 60 is positioned proximal to an enlarged distal portion of outer shaft 11, as shown in FIG. 43. As shown, channel 63 within drill guide 60 is sized so that drill guide 60 fits over outer shaft 11. Drill guide 60 is then slid axially in a distal direction toward the attached implant 700, as indicated by reference numeral 94 in FIG. 43. As drill guide 60 passes over button 20, button depresses so that drill guide may pass over it. Alternatively, the user may press the button down prior to advancing the drill guide over. Pressing of the button compresses springs 22A, 22B beneath it allowing button downward into a space beneath it temporarily while load is applied. At the same time, and as shown in part in FIG. 44, rails 64A, 64B of drill guide 60 are slidably received in corresponding slots 26A, 26B on outer shaft 11. Drill guide 60 continues to be advanced until edge 75 is distal to and no longer over button 20. Once drill guide 60 is past button 20, button 20 springs outward and returns to its unbiased, expanded position as shown in FIGS. 44 and 45. When drill guide 60 reaches this position, it is fully seated in and captured by insertion tool 10. In a distal direction, rails 64A, 64B abut ends 27A, 27B of the slots along sides of outer shaft 11 to prevent further distal movement. In the proximal direction, drill guide 60 is prevented from backing out of insertion tool by button 20 protruding from outer shaft 11 surface. Through the slidable engagement between rails and slots, drill guide is also prevented from disengaging in an upward direction as well. It should be appreciated that, although not shown, slot 26B is equal and directly opposite slot 26A.

With the above steps completed, the implant is ready for placement in an intervertebral space of a patient and/or for the drilling of fasteners with a driver tool positioned through bores of drill guide into corresponding openings in the implant. The drill guide may be removed from the insertion tool at any time by pressing down on button 20 and then sliding drill guide 60 over button 20 axially in a proximal direction.

The above method illustrates that the combination of an insertion tool and a drill guide as described is advantageous because the insertion tool may be used to insert an implant, but that it may also be used with a size specific drill guide that may be attached to the insertion tool. Further, the drill guide may be attached to the insertion tool prior to placing the implant in the intervertebral space or after the implant is in its intended placement location in the spine.

Figure 46:
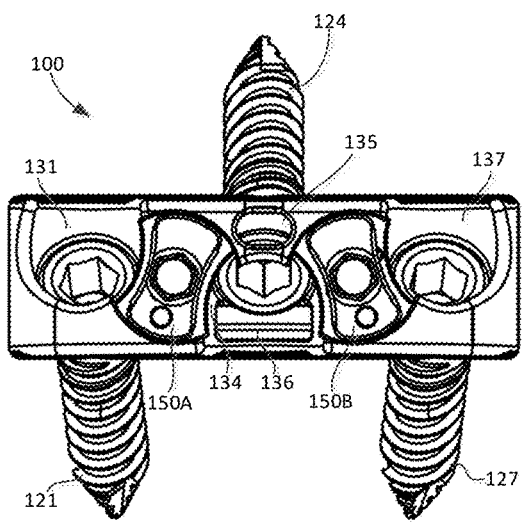
FIGS. 46-49 are side views of an intervertebral implant in steps of a method of locking fasteners of the intervertebral implant according to another embodiment of the disclosure.
Figure 48:
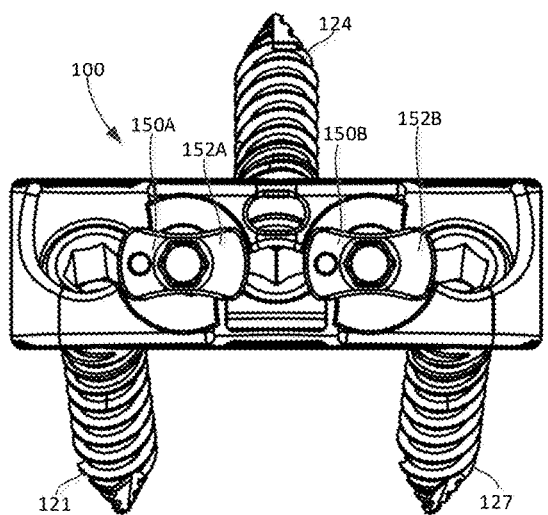

In another aspect, fasteners in an implant are locked using locking elements. In one embodiment, implant 100 is secured in place within an intervertebral space through the seating of fasteners 121, 124, 127 as shown in FIG. 46 into vertebral bodies adjacent to the vertebral space. The fasteners may be seated one at a time through the use of a driver element, for example. Although fasteners with particular features are shown in the figures, it is contemplated that other fasteners may be used to secure the implant within the intervertebral space. To preserve the fasteners seated position, locking elements 150A, 150B are both rotated in a clockwise direction to move the locking elements from a first locked position shown in FIG. 46 to a second locked position shown in FIG. 48. As FIG. 46 shows, in the first locked position, neither locking element 150A, 150B blocks any of the fasteners. However, as FIG. 48 shows, in the second locked position, head 152A blocks fasteners 121, 124 and head 152B blocks fasteners 124, 127. In this manner, fasteners 121, 124, 127 are covered and thereby blocked from backing out of implant 100. The position of the locking element relative to the body may also be referred to as its orientation.

Figure 47:
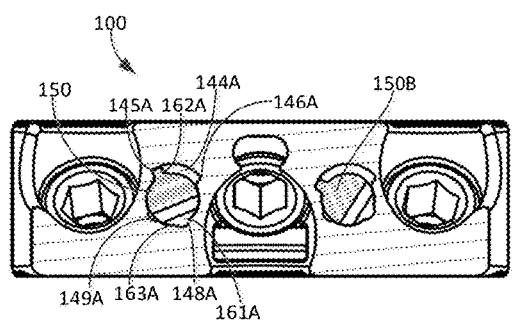
Figure 49:
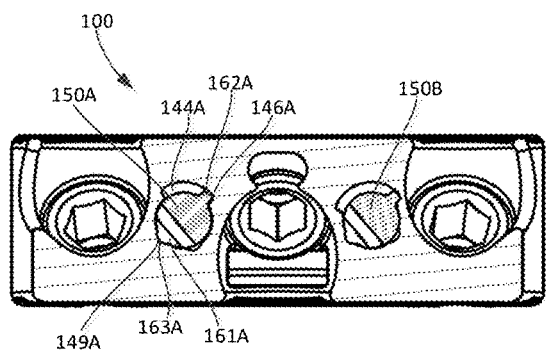

Details of how locking elements 150A, 150B interact with the implant structure to move from the first locked to the second locked position are shown in FIGS. 47 and 49, where FIG. 47 illustrates the first locked position and FIG. 49 illustrates the second locked position. With locking element 150A referenced as illustrative, in the first locked position, ridge 162A of base element is located at first location 145A on the perimeter of second recessed surface 144A, at an end of the area defined by the second radius. On an opposite side of the base of locking element 150A is protrusion 163A, which is disposed in first groove 148A. When locking element 150A is rotated in a clockwise direction, flexible bar 161A bends inward upon disengagement from first groove 148A so that flexible bar 161A fits within second recessed surface 144A as it rotates toward second groove 149A. Once rotation brings protrusion 163A over second groove 149A, flexible bar 161A expands into its neutral state and protrusion 163A snaps into second groove 149A to establish the second locked position, as shown in FIG. 49. Simultaneously, ridge 162A rotates along second radius of second recessed surface from first location 145A until it approaches an end of the arc at second location 146A. One function of the end surfaces abutting second recessed surface 144A at the first and second locations is to prevent locking element 150A from over-rotating. By way of example, if clockwise rotation of locking element 150A were to rotate protrusion 163A past the second groove, further rotation would be prevented because ridge 162A is blocked from further rotation by the end surface at second location 146A, as shown in FIG. 49. The method described immediately above for implant 100 may be performed in the same manner for implant 700.

The design of locking elements 150A-B, 750A-B is advantageous because it provides visual, tactile and audible feedback to the user to confirm that the locking elements are in a locked position. Visual feedback is provided by knowledge that an observation of each locking element in a horizontal position indicates that each locking element is locked, as shown, for example, in FIG. 48. Further, the visualization feature is present even where the implant is a size other than that depicted. Tactile feedback is provided by the flexible bar as it moves from an intermediate position into either locked position, i.e., blocking the fasteners in FIG. 48 or clear of the fasteners in FIG. 46. For example, when protrusion 163A snaps into a respective groove 149A on the anterior surface, the user experiences a "pop" sensation. Audible feedback is provided through the use of a torque-limiting cam lock driver to lock the locking element. When a locking element reaches a locked position, the lock driver breaks away from the locking element and the breakage makes a sound. At the same time, the user senses the breakage of the lock driver, another form of tactile feedback.

Figure 50:
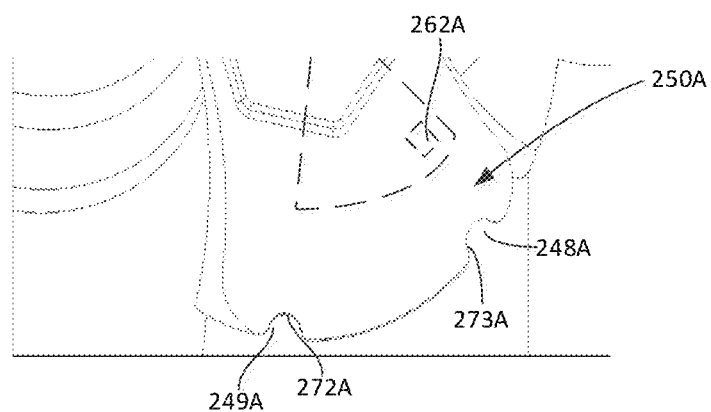
FIGS. 50-51 are close up partial side views of an intervertebral implant in steps of a method of locking fasteners of the intervertebral implant according to another embodiment of the disclosure.
Figure 51:
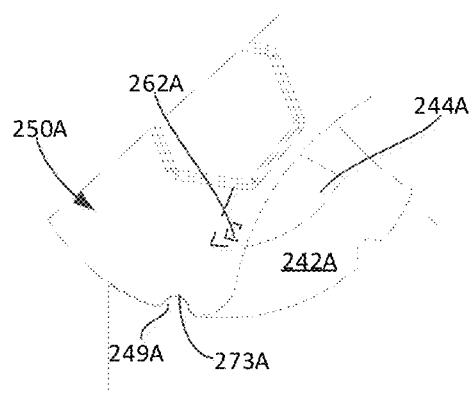
Figure 52:
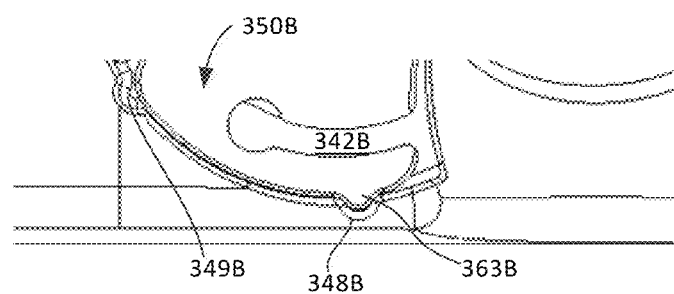
FIGS. 52-53 are close up partial side views of an intervertebral implant in steps of a method of locking fasteners of the intervertebral implant according to another embodiment of the disclosure.
Figure 53:
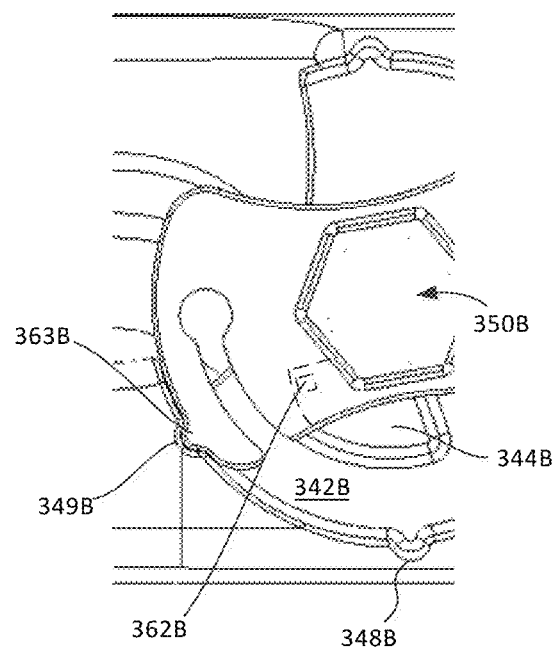

The method shown in FIGS. 46-49 may also be performed with implant 200, as shown in FIGS. 50-51 and with implant 300, as shown in FIGS. 52-53. With implant 200, FIG. 50 shows a first locked position of locking element 250A. In this position, both grooves 272A, 273A on head 252A are engaged with inward bumps 248A, 249A on an edge of first recessed surface 242A. When rotated into the second locked position of FIG. 51, only groove 273A remains engaged to implant 200 at bump 249A. Shown in hidden lines is inner protrusion 262A, the movement of which is limited by an outer dimension of second recess 244A to prevent over-rotation of locking element 250A. Turning to implant 300, when locking element 350B is disengaged from the first locked position of FIG. 52, flexible bar 361B bends inward while locking element 350B rotates in a first direction until protrusion 363B snaps into second groove 349B, as shown in FIG. 53. Again, during rotation, ridge 362B under head 352B limits over-rotation. Although not shown, in this configuration, a pair of locking elements are rotated in opposite directions to move toward a desired position. Thus, where locking element 350B is rotated in a first direction to move into the locked position, locking element 350A (not shown) is rotated in a second direction opposite the first.

In yet another embodiment, the method of attaching the implant and the drill guide to the instrument are performed together with the securement of the implant in an intervertebral disc space and locking of the locking elements of the implant, as described above, as a single method.

Figure 54:
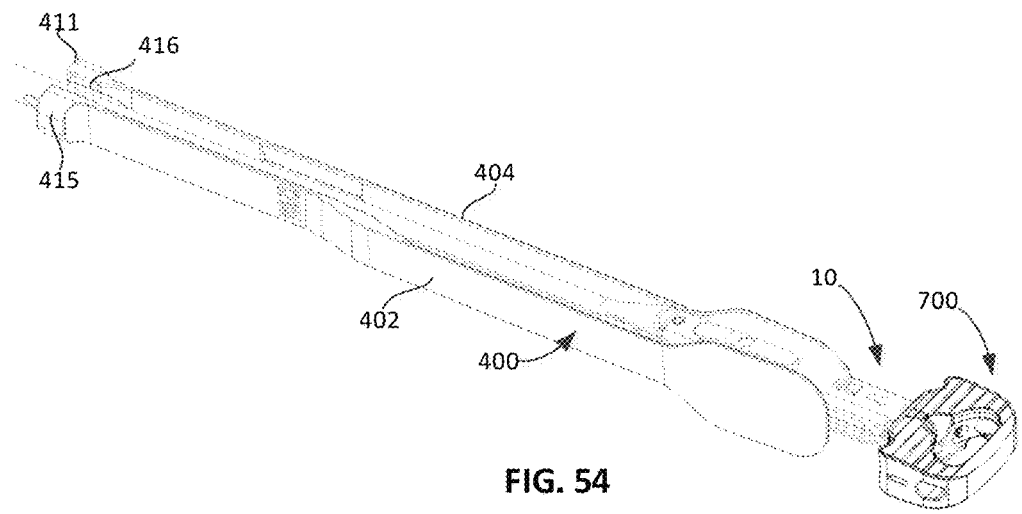
FIGS. 54-56 are various views of an insertion tool and graft clip in steps of a method of securing the graft clip to the insertion tool according to another embodiment of the disclosure.
Figure 55:
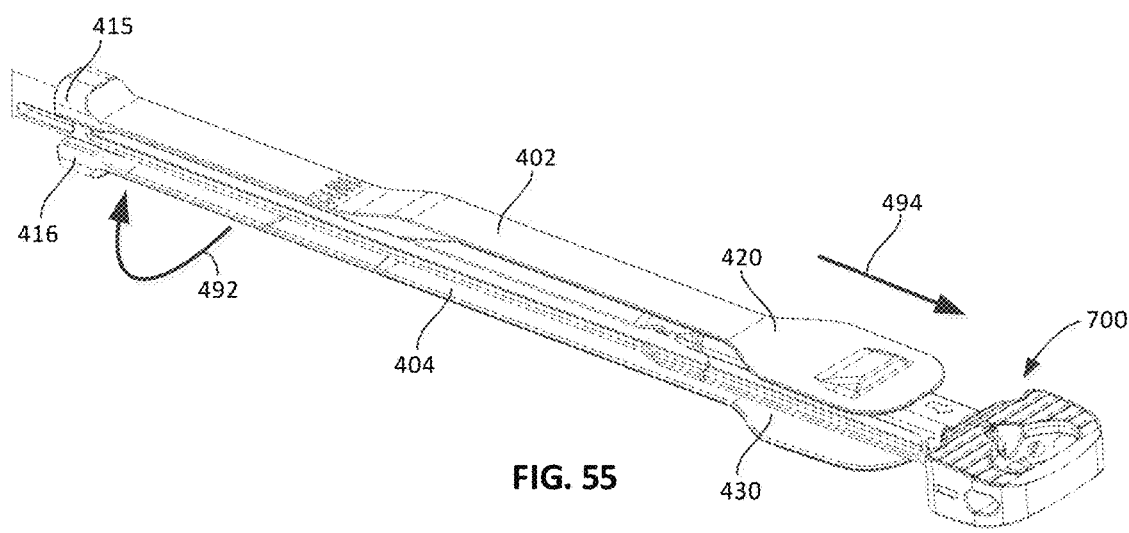
Figure 56:
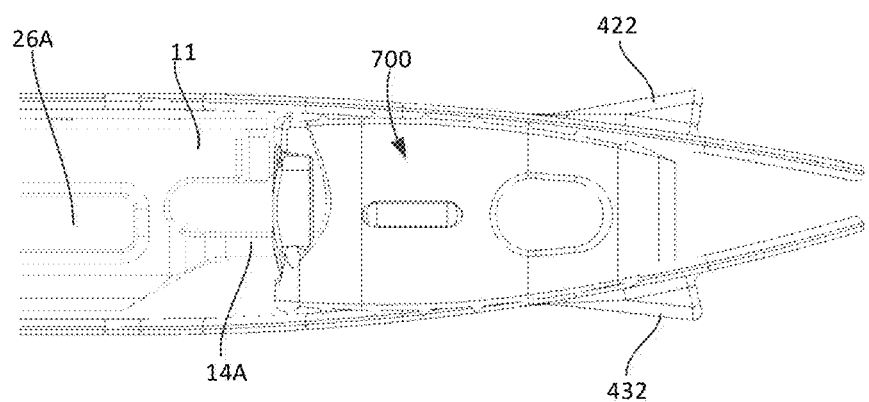

In another embodiment, the method involves steps corresponding to FIGS. 37 through 42, after which the implant is advanced into an intervertebral space for implantation. In yet another embodiment, implant 700 is secured to insertion tool 10, and then graft clip 400 is attached to both. The attachment of graft clip 400 is illustrated in FIGS. 54-56. Initially, an open side of graft clip is directed over outer shaft 11, as shown in FIG. 54. Then, once graft clip covers outer shaft, graft clip 400 is rotated about ninety degrees in a counterclockwise direction when facing away from the user at the proximal end, as indicated by reference numeral 492. The rotation snaps graft clip 400 into place on the insertion tool 10 via the inner surfaces 415, 416 at proximal end 411. Graft clip 400 is then slid down outer shaft as indicated by reference numeral 494 until paddles 420, 430 cover implant 700, as shown in FIG. 56. The operative position of graft clip 400 relative to implant 700 shown in FIG. 56 is exemplary, though it is envisioned that distal end 412 of the graft clip may be positioned closer to or further from a distal end of implant 700. The preparation of the insertion tool is now completed for use in insertion of the implant into the spine.

In some variations, the method may include further steps of insertion of the tool with the graft clip attached. When inserted into a disc space as a complete assembly as shown in FIG. 56, the upper and lower stops 420, 430 bottom out on the bone of the vertebrae adjacent to the target disc space while implant 700 continues to be advanced as much as necessary to position it in a final implant location. One advantages of this approach is that it minimizes dislodging of bone graft in the implant during impaction of the implant into the disc space. The method also allows for access into smaller disc spaces than would otherwise be possible. Additionally, the tapered distal ends of each arm provide an improved lead-in to the target disc space.

It should be noted that any of the devices and methods disclosed herein can be used in conjunction with robotic technology. For example, the insertion tool described herein can be used with robotic surgical systems to perform an implant insertion procedure. The insertion tool can be manipulated with a robotic system or a robotic arm to rotate, position, and actuate the lever arm of the insertion tool during a procedure. Further, any or all of the steps described in the methods for performing an implant insertion or securement procedure of the present disclosure may be performed using a robotic system.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A system comprising:
an insertion tool comprising:
a body having a distal portion and a distal end, the body including a first engagement feature extending longitudinally along the distal portion; and
two arms extending longitudinally from the distal end of the body; and
a drill guide including two bores and an open faced channel therebetween, the open faced channel including a second engagement feature slidably engageable with the first engagement feature on the body of the insertion tool,
wherein the two bores are adapted for the disposal of a fastener driver tool therethrough.

2. The system of claim 1, wherein the insertion tool further comprises a pin that extends longitudinally from the distal end of the body.

3. The system of claim 2, wherein the first arm and the second arm have equal and opposite shapes and the pin has a shape different from each of the first arm and the second arm.

4. The system of claim 3, wherein a first plane passes through a central longitudinal axis of the body and a length of the pin such that each of the first arm and the second arm are entirely offset from the first plane.

5. The system of claim 2, wherein the first arm includes a first protrusion thereon and the second arm includes a second protrusion thereon, the first and second arms having a first length and the pin having a second length less than the first length.

6. The system of claim 1, wherein the first arm and the second arm are biased inward toward one another.

7. The system of claim 1, wherein the first engagement feature is a pair of slots on opposite surfaces of the body of the insertion tool and the second engagement feature is a pair of rails facing one another, each of the rails disposable within respective slots of the body.

8. The system of claim 1, wherein the insertion tool further comprises an actuatable button on the distal portion of the body, the actuatable button biased to protrude relative to the body.

9. The system of claim 8, wherein the drill guide is adapted to slide over the actuatable button while one of the first engagement feature and the second engagement feature is disposed in the other, the drill guide secured to the insertion tool when positioned in between the actuatable button and the distal end of the body.

10. The system of claim 1, wherein the body is cannulated and includes a slidable element disposed therein, the insertion tool being actuatable to advance and retract the slidable element.

11. An intervertebral implant comprising:
a body with a plurality of openings therein, each of the plurality of openings being accessible from a single side of the body;
a fastener disposed in a first opening of the plurality of openings; and
a locking element disposed in a second opening of the plurality of openings comprising:
a head;
a flexible base abutting the head; and
a shaft extending from the flexible base, wherein the flexible base and the shaft extend along a longitudinal axis, wherein the flexible base is movable from a first position to a second position such that in the first position the flexible base is secured to the body and has a first perimeter and in between the first position and the second position, a portion of the flexible base is deformed so that the flexible base has a second perimeter smaller than the first perimeter, the first perimeter and the second perimeter measured at the same axial location on the flexible base, and wherein the locking element is movable between a first orientation relative to the body that blocks the first opening and a second orientation relative to the body that does not block the first opening.

12. The intervertebral implant of claim 11, wherein the flexible base includes a flexible bar that extends from a remainder of the flexible base to a free end such that the flexible bar is separated from the remainder of the flexible base by a space.

13. The intervertebral implant of claim 12, wherein the flexible bar includes a protrusion extending outward adjacent to the free end.

14. The intervertebral implant of claim 13, wherein the single side of the body includes a first recessed surface sized to receive the head of the locking element and a second recessed surface that is recessed relative to the first recessed surface, the second recess sized to receive the flexible base.

15. The intervertebral implant of claim 14, wherein the second recessed surface includes a perimeter defined by a first portion with a first radial dimension and a second portion with a second radial dimension smaller than the first radial dimension, the second portion interrupted by a first groove and a second groove spaced from one another along a partially circumferential length of the second portion.

16. The intervertebral implant of claim 15, wherein when the locking element is disposed in the implant such that the head is disposed on the first recessed surface, the locking element is rotatable such that the protrusion of the flexible bar is disposable in the first groove and in the second groove.

17. The intervertebral implant of claim 16, wherein when the protrusion is disposed in the first groove, a ridge on the base abuts a first end of the first portion of the perimeter of the second recessed surface and when the protrusion is disposed in the second groove, the ridge on the base abuts a second end of the first portion of the perimeter of the second recessed surface.

18. The intervertebral implant of claim 12, wherein the flexible bar includes a protrusion extending outward adjacent to the free end and the flexible base includes a longitudinal ridge, the longitudinal ridge positioned opposite the protrusion on a surface of the flexible base.

19. The intervertebral implant of claim 11, wherein the shaft is a pair of flexible prongs.

20. An intervertebral implant comprising:
a body with a plurality of openings therein, each of the plurality of openings being accessible from a first side of the body, the first side having a first recessed surface and a second recessed surface;
a fastener disposed in a first opening of the plurality of openings; and
a locking element disposed in a second opening of the plurality of openings, the second opening being located entirely within the second recessed surface, the locking element comprising:
a head;
a flexible base abutting the head, the flexible base including a first part and a second part separated from the first part by a third opening, the first part extending to a free end and having a protrusion, and the second part having a ridge; and
a shaft extending from the flexible base, the shaft and the flexible base extending along a longitudinal axis, wherein the flexible base is movable from a first position to a second position such that in the first position, the protrusion is engaged with a groove defined by a boundary between the first recessed surface and the second recessed surface and the ridge abuts a radially oriented edge of the second recessed surface and in the second position, the first part of the flexible base is compressed from a neutral position and is outside of the groove, and wherein the locking element is movable between a first orientation relative to the body that blocks the first opening and a second orientation relative to the body that does not block the first opening.

\* \* \* \* \*